United States Patent
Halldin et al.

(10) Patent No.: US 6,951,460 B2
(45) Date of Patent: Oct. 4, 2005

(54) COMPONENTS AND METHOD FOR IMPROVED IMPRESSION MAKING

(75) Inventors: Anders Halldin, Göteborg (SE); Kent Engström, Malmö (SE)

(73) Assignee: Astra Tech AB, Mölndal (SE)

( * ) Notice: Subject to any disclaimer, the term of this patent is extended or adjusted under 35 U.S.C. 154(b) by 419 days.

(21) Appl. No.: 09/985,141

(22) Filed: Nov. 1, 2001

(65) Prior Publication Data

US 2003/0082499 A1 May 1, 2003

(51) Int. Cl.[7] .................................................. A61C 8/00
(52) U.S. Cl. ...................... 433/173; 433/213; 433/214
(58) Field of Search ................................ 433/172, 173, 433/174, 176, 213, 214

(56) References Cited

U.S. PATENT DOCUMENTS

| | | | |
|---|---|---|---|
| 3,304,608 A | 2/1967 | Frohnecke | |
| 4,177,562 A | 12/1979 | Miller et al. | 433/174 |
| 4,253,833 A | 3/1981 | Edelman | 433/173 |
| 4,575,340 A | 3/1986 | Lustig | 433/173 |
| 4,738,623 A | 4/1988 | Driskell | 433/173 |

(Continued)

FOREIGN PATENT DOCUMENTS

| | | |
|---|---|---|
| DE | 31 10693 A1 | 9/1982 |
| EP | 0 190 670 A2 | 8/1986 |
| EP | 0 814 724 B1 | 1/1998 |
| EP | 0 879 025 B1 | 11/1998 |
| WO | WO 96/29019 | 9/1996 |
| WO | WO 98/32393 | 7/1998 |
| WO | WO 02/17814 A1 | 3/2002 |

OTHER PUBLICATIONS

Brochure by Straumann Dental "Prosthetic Info", Crown and bridge restorations, Nov. 1999, Waldenburg, Switzerland.
Brochure, "TG OSSEOTITE/ITI Impression Procedure Comparison", 3i Implant Innovations, Inc. (Rev. Jan. 2001).
Brochure, "TG Post Restorative Guidelines Laboratory Procedure", 3i Implant Innovations, Inc.

Primary Examiner—Cary E. O'Connor
(74) Attorney, Agent, or Firm—Birch, Stewart, Kolasch & Birch, LLP

(57) ABSTRACT

The invention relates to components for an improved system for pick-up impression making at a dental implantation site, including an abutment, an abutment replica and an impression coping. The invention also relates to a series of abutments and to a set comprising an abutment and an impression coping. The impression coping has a through passage extending from a coronal end to an apical end of the impression coping and includes an abutment surrounding region for surrounding the abutment. The abutment surrounding region has a coronal end, an apical end and an inner wall. The inner wall includes at least one abutment contact surface for contact with the abutment, and at least one space forming surface for being spaced apart from the abutment in order to provide a space between the space forming surface and the abutment.

29 Claims, 18 Drawing Sheets

U.S. PATENT DOCUMENTS

| | | | |
|---|---|---|---|
| 4,955,811 A | 9/1990 | Lazzara et al. | 433/173 |
| 4,995,810 A | 2/1991 | Söderberg | 433/141 |
| 5,125,841 A | 6/1992 | Carlsson et al. | 433/213 |
| 5,297,963 A | 3/1994 | Dafatry | 433/172 |
| 5,334,024 A | 8/1994 | Niznick | 433/173 |
| 5,376,004 A | 12/1994 | Mena | 433/173 |
| 5,662,476 A | 9/1997 | Ingber et al. | 433/213 |
| 5,685,715 A | 11/1997 | Beaty et al. | 433/173 |
| 5,688,123 A | 11/1997 | Meiers et al. | 433/173 |
| 5,733,124 A * | 3/1998 | Kwan | 433/173 |
| 5,762,500 A | 6/1998 | Lazarof | 433/213 |
| 5,779,480 A | 7/1998 | Groll et al. | 433/173 |
| 5,816,809 A | 10/1998 | Sapkos | 433/172 |
| 5,829,981 A | 11/1998 | Ziegler | 433/214 |
| 5,899,695 A | 5/1999 | Lazzara et al. | 433/173 |
| 5,899,697 A | 5/1999 | Lazzara et al. | 433/173 |
| 5,904,483 A | 5/1999 | Wade | 433/173 |
| 5,938,443 A | 8/1999 | Lazzara et al. | 433/173 |
| 5,964,591 A | 10/1999 | Beaty et al. | 433/173 |
| 6,068,478 A | 5/2000 | Grande et al. | 433/172 |
| 6,120,293 A | 9/2000 | Lazzara et al. | 433/173 |
| 6,142,782 A | 11/2000 | Lazarof | 433/174 |
| 6,149,433 A | 11/2000 | Ziegler et al. | 433/214 |
| 6,155,828 A | 12/2000 | Lazzara et al. | 433/173 |
| 6,159,010 A | 12/2000 | Rogers et al. | 433/172 |
| 6,332,777 B1 * | 12/2001 | Sutter | 433/173 |
| 6,488,501 B1 | 12/2002 | Harding | |
| 2002/0106610 A1 * | 8/2002 | Hurson | 433/173 |

* cited by examiner

COMPONENTS AND METHOD FOR IMPROVED IMPRESSION MAKING

BACKGROUND OF THE INVENTION

1. Field of the Invention

The invention relates to components for an improved system for pick-up impression making at a dental implantation site, comprising an impression coping and an abutment replica. The invention also relates to a set comprising an abutment and an impression coping and to a method for impression making.

2. Description of Related Art

Dental implant systems are widely used for replacing damaged or lost natural teeth. In such systems, an implant is placed in the jaw of a patient in order to replace the natural tooth root. An abutment structure comprising one or several parts may then attached to the implant in order to build up a core for the part of the prosthetic tooth protruding from the bone tissue, through the soft gingival tissue and into the mouth of the patient. On said abutment, the prosthesis or crown may finally be seated.

The final prosthesis must be sized and configured so as to naturally fit with the remaining teeth of the patient, both for functionality and aesthetics. To this end, a dental technician needs to try out a proper prosthesis for the individual patient, using a model of the jaw of the patient, said model including the implant and possibly an abutment structure. To provide such a model, so-called master cast modelling techniques are used.

One category of such modelling techniques is the so-called "pick-up" method. A pick-up method could be described by the following subsequent steps:

An impression cap is placed on the implant and/or the abutment.

An impression material is applied to the jaw, such that said impression cap is embedded in the impression material.

The impression material is removed from the jaw, bringing along the impression cap still being embedded in the impression material. The impression material now has the inverse form of the jaw with the impression cap at the site of the implant/abutment.

A replica replicating the shape of the implant and/or abutment is inserted into the embedded impression cap, in the same manner as the original implant and/or abutment was connected to the impression cap.

A molding material is poured into the inverse form of the jaw made out of the impression material and around the replica and let to harden.

The impression material is removed from the hardened molding material, said molding material now forming a true, or non-inverse model of the jaw with the replica replacing the original implant/abutment.

In the following, reference will be made to some prior art documents describing pick-up methods or components to be used therewith.

U.S. Pat. No. 6,068,478 (Grande et al.) discloses an impression system including an impression cap for transferring an end, protruding from a human tissue structure, of an implant which is fitted in the human body, including possible superstructures, to a master cast. The outwardly directed implant end has an undercut contour on its outside, and the impression cap has a geometry which complements the undercut contour and engages therein. The undercut contour is formed either by an implant geometry tapering in a trumpet shape towards the implant bed, or by a recess near the implant end.

In said U.S. Pat. No. 6,068,478 (Grande et al.), a superstructure part is described to be screwed into the implant such that an abutment of the superstructure is projecting above the implant shoulder. For taking an impression of the mouth situation to a finished master cast, a slide sleeve is first of all pushed onto the conical superstructure. Then, an impression cap is pushed over the slide sleeve. At the very bottom, the impression cap has a cap shoulder, which is complementary to the implant shoulder. On the outside, the cap shoulder is surrounded by an elastic snap element directed inwards, so that it can snap over the implant shoulder and releasably grip an undercut contour on the implant head. An impression tray filled with impression compound is now pressed onto the implantation site. After withdrawing the impression tray, the impression cap and the slide sleeve remain embedded in the impression compound, and the impression is obtained. An analogous manipulation implant having a shape corresponding to the conical superstructure is now pushed into the slide sleeve. Finally, a manipulation shoulder sleeve, having a manipulation shoulder corresponding to the implant shoulder is pushed over the manipulation implant until the manipulation shoulder is held by the snap element of the impression cap. Modelling compound is lastly poured onto the impression and the master cast is obtained.

In said U.S. Pat. No. 6,068,478 (Grande et al.), another impression method is used if another type of superstructure, for example an angled superstructure is attached to an implant. In this case, an impression cylinder is screwed onto the superstructure and a laterally open impression cap is pushed onto the superstructure such that is grabs the implant shoulder. The impression is taken using the impression tray filled with impression compound, which impression is obtained after withdrawing the impression tray, and in which the impression cap and a hollow space according to the impression cylinder and the conical superstructure remain behind. In the next step, the impression cylinder is pushed into its hollow space and the manipulation shoulder sleeve is attached, and modelling compound is then filled through the manipulation shoulder sleeve so that the whole hollow space is filled up. Modelling compound is now poured onto the impression and, after removing the impression tray in which the impression cylinder remains, the finished mater cast is obtained.

It is further mentioned that the slide sleeve might be omitted if the hollow space remaining in the impression cap, and left by the selected abutment inside the impression cap, is filled with impression compound. Also, the slide sleeve and the impression cap may be combined and designed as one piece.

U.S. Pat. No. 6,159,010 (Rogers et al.) discloses a dental coping for placement over an abutment post that is attached to and protruding above a dental implant. The coping includes a base portion having an internally tapered surface for mating with a support surface of the implant. A wall extends away from the base portion for enveloping the abutment post. The wall includes at least one aperture for allowing wax material to pass therethrough when taking an impression of the implantation site.

U.S. Pat. No. 5,688,123 (Meiers et al.) discloses a transfer cap for dental implants that is to be used when taking an impression for forming a master cast model. This transfer cap is adapted in form and size to the built-up part or abutment of the implant and carries one or more resilient flaps extending over the shoulders of a conical area of the built-up part.

WO 99/29255 (Morgan) discloses an abutment analogue having a head portion being formed with retention means such as an annular groove.

EP 0 190 670 (Lustig) discloses a prefabricated abutment that may be used in combination with a prefabricated sleeve-like coping which is telescopically mated to the post.

An object of this invention is to provide components for a system for improved function when using pick-up impression methods, and a method using said components.

SUMMARY OF THE INVENTION

According to a first aspect of the invention, there is provided an impression coping for pick-up impression making of a dental abutment attached to a dental implant, said impression coping having a through passage from an apical and to a coronal end of the impression coping. The impression coping comprises an abutment surrounding region for surrounding said abutment, said abutment surrounding region having an apical end and a coronal end and an inner wall, comprising at least one abutment contact surface for contact with said abutment, and at least one space forming surface for being spaced apart from said abutment in order to provide a space between said space forming surface and said abutment.

The term "coronal" is here and throughout this application used to indicate a direction towards a head end or trailing end of the component discussed. For example, in a situation where an abutment is connected to an implant, the coronal direction would be a direction towards the part of the abutment being directed away from the implant. Likewise, the term "apical" indicates a direction towards an insertion end of the component. For an abutment connected to an implant, the apical direction would be a direction towards the implant. Thus, apical and coronal are opposite directions.

However, if parts of a component or a system are angulated in relation to each other, the apical and coronal directions of the different parts, respectively, may not be coinciding. For example, this would be the case for an abutment where the component support region of an abutment is angled in relation to the implant contacting region, a so called angled abutment. Herein, when discussing the apical direction of the component support region, a direction towards the maximum diameter of the component support region is referred to. The coronal direction of a component support region is a direction away from said maximum diameter, towards a free end of the component support region.

Preferably, the impression coping is having a through passage extending from a coronal end to an apical end of the impression coping. This is advantageous since impression material may then be introduced through the coronal end into the impression coping, thus increasing the fixation of the impression coping in the impression material. Impression material introduced into the impression coping will contact part of the abutment, and thus provide an open space replicating said abutment part. This open space may be used for guiding the later introduction of an abutment replica, or as will be described in the detailed part of the description, as a form for forming a model of a customised abutment.

Further, impression material may be introduced in said space between said space forming surfaces and said abutment. However, there are also abutment contact surfaces, that contacts the abutment thus providing a stable contact surface.

When taking an impression of a standard abutment, the abutment contact surfaces will contact the standard abutment. Impression material may optionally be introduced into the spaces formed by the space forming surfaces, but this is not necessary. The abutment contact surfaces will namely normally provide enough surface to guide the later insertion of an abutment replica into exactly the same position as the abutment had inside the impression coping.

However, when taking an impression of a modified abutment, all of the abutment contact surfaces will probably not be in contact with the modified abutment. At least a portion of the abutment contact surfaces will most likely not contact the customised abutment, due to the modified shape thereof. In this case a composite space is formed between the abutment and the inner wall of the impression coping, said composite space being composed by a space created between the abutment contact surface and the modified abutment and said space between said space forming surface and said abutment. Impression material may be introduced into the impression coping and into the composite space formed between said impression coping and the modified abutment. Thus, when removed from the abutment, the impression material together with the impression coping will form an empty space having an inner "modified" shape corresponding to the shape of the modified abutment, said inner shape being subsequently used for molding a model of said modified abutment.

Preferably, said space forming surface may be provided with a vent for passage air from said composite space. Thus, when impression material is introduced into said composite space, air may flow through the space formed between said space forming surface and said abutment out through the vent, whereby air bubbles are avoided and proper introduction of impression material is ensured. The space forming surface thus provides an air duct for air evacuation from said composite space.

The vent may be provided by an opening in the space forming surface or possibly by a perforation or other suitable vent means.

Naturally, the abutment may alternatively be modified such that all of the abutment contact surface is still in contact with the modified abutment, and the composite space is related only to the space forming surfaces. The extent to which said composite space needs filling with impression material is dependent on the modification made of the abutment. However, complete filling may normally be ensured by having impression material filled into the entire composite space and flowing out of said vent.

Advantageously, at least one abutment contact surface may be tapering inwardly in a coronal direction. This is particularly useful when the impression coping is to be seated on an abutment having a tapered outer shape.

The impression coping is thus useful both for taking impressions of a standard abutment and of a modified standard abutment. This provides advantages over prior art, where different components are often used for standard and customised situations.

In a first variant of said impression coping, the abutment surrounding region of the impression coping comprises a shoulder contacting portion having an inner wall and a post surrounding portion extending coronally from said shoulder contacting portion and presenting an inner wall forming an angle larger than 180° with said inner wall of said shoulder contacting portion.

The shoulder contacting portion is intended to contact a shoulder portion of a corresponding abutment. Accordingly, the projection of a normal to the outer surface of said shoulder contacting portion onto a longitudinal axis of the component surrounding region would extend in the apical direction.

The post surrounding portion may have an inner wall having various shapes. It may be formed such that the entire inner wall contacts a post portion of an abutment. However, it may also be formed so as to contact the post portion of an abutment only with a part of said inner wall. Some such embodiments will be described below.

Further, the shoulder contacting portion is useful for increasing contact and stability in the interaction with said abutment. This is particularly important as the impression coping will be used in pick-up impression methods, where it will first be attached to an abutment being fixed to an implant, thereafter embedded in impression material and removed from the abutment together with said impression material, and finally an abutment replica will be inserted into said impression coping. For succeeding with this method, both the abutment and the abutment replica should be securable in the impression coping with great accuracy, to which said shoulder contacting portion contributes.

Also, the combination of a shoulder contacting portion and post contacting surfaces provides a possibility of ensuring that the impression coping is correctly placed on the abutment. In some prior art systems there are provided impression caps having only a shoulder contacting portion and a post surrounding portion with no abutment contact surfaces. Such prior impression caps risk however being incorrectly placed on the abutment.

According to an embodiment of said first variant of the first aspect of the invention, the impression coping is further provided with releasable abutment engagement means being provided apically of at least one space forming surface. Preferably, said abutment engagement means are provided at the post contacting portion, at a position being closer to the shoulder contacting portion than to the coronal end of the abutment surrounding region.

In said embodiment of the impression coping, the placement of the abutment engagement means on the inner wall of a post contacting portion extending from a shoulder contacting portion results in a position of the locking means where the diameter of the abutment on which the impression coping is to be seated is relatively small, as compared to the diameter at a shoulder portion of the abutment. Thus, this placement of the locking means allow more construction variations of the locking means to be used without having to increase the outer diameter of the impression coping at the locking means beyond the maximum diameter of said abutment.

A small outer diameter of the impression coping is advantageous. When having a large diameter, the mucosa surrounding the abutment or implant to which the impression cap is set must be pushed aside and risks being damaged. Further, a large diameter of an impression cap makes it difficult to attach or remove the component without colliding with the teeth adjacent to the implant. Where the adjacent teeth are very close set, the diameter of the component might even be too large for the component to pass between the teeth to be set on the abutment. However the arrangement disclosed above diminishes these problems.

In prior art systems, locking means such as flaps are sometimes provided at the end of an impression cap for engagement over and around an abutment. In these constructions, the locking means will contribute to an enlarged outer diameter of the impression cap, leading to unnecessary compression of the soft gingival tissue surrounding the abutment. Further, the placement of the locking means at the end of the impression caps often leads to a low attachment level of the cap down in the gingival tissue of the patient.

In other prior systems there are locking means provided close to the coronal end of the impression cap. These systems have the disadvantage that the abutment on which the impression cap is to be seated may not be modified below said coronal end, if the impression cap shall still be attachable to the abutment.

The abutment engagement means may be provided at a transition between said post contacting portion and said shoulder contacting portion. Further, the abutment engagement means may comprise at least one protrusion or indentation, such as a groove or rib, in an inner wall of said abutment surrounding region.

At least one abutment contact surface may be provided with a rotational locking means, for rotational locking of said impression coping on said dental abutment. This feature is useful for ensuring a proper transfer of the rotational direction of the abutment fixed to the implant to a master cast model via impression making.

For enhanced attachment into the impression material, the impression coping may be provided with a prolongation region coronally of the abutment surrounding region. Such a prolongation region will also make the impression coping easier to handle. Said prolongation region may further be provided with retention elements for retention of the impression coping in an impression material.

According to a second aspect of the invention, there is provided a set comprising an abutment and an impression coping as above.

In a third aspect of the invention, there is provided an abutment replica, comprising a component support portion replicating the component supporting region of an abutment, and an apical region having an apical end, wherein a bore is extending from said apical end into the abutment replica, at least to a position being in level with said component support region.

This replica has the advantage that at least part of the component support region may be cut off leaving a replica comprising the apical region and possibly a part of the support region and being provided with a through bore. This possibility is used when making a master cast of a modified abutment, which will be described in more detail in the specified part of the description. The replica according to this embodiment is advantageous since it may be used both for situations where the abutment is left in its standard appearance (in its original state) and for situations where the abutment is modified (in a cut-off state).

As such, the abutment replica is particularly advantageous for use together with the impression coping according to the first aspect of the invention, since also the impression coping is useful for both situations where the abutment is left in its standard appearance and for situations where the abutment is modified.

In an embodiment of the abutment replica, it is further provided with abutment engagement means for connection to a dental component, wherein said bore extends from said apical end into the abutment replica, at least to a position coronally of said abutment engagement means.

Thus, a part of the component support region extending coronally of the locking means may be cut off, revealing a bore extending through the entire remaining portion of the abutment replica, which is also having the abutment engagement means intact.

In a fourth aspect of the invention there is provided a set comprising an abutment having a coronal abutment end and a corresponding replica having a coronal replica end, said abutment being provided with a marking for optional shortening of the abutment at a first distance from the coronal abutment end, wherein said replica is provided with a marking at a second distance from the coronal replica end being equal to or less than said first distance.

The markings proposed according to said fourth aspect of the invention may be used to further increase the possibilities of simply modifying the system. If a shorter than standard abutment is desired, a standard abutment may be cut off at a marking. The replica used in subsequent model making has a correspondent marking at a distance from the coronal end of the replica equal to or less than the distance between the marking of the abutment and a coronal end of the abutment. After cutting off the replica at said marking there is provided a cut-off replica having a height being equal to or greater than the height of the cut-off abutment. In the model, a suitable prosthesis is built up on the replica and thereafter transferred to and attached to the cut-off abutment. The fit of the prosthesis on the abutment is ensured by the locking of the prosthesis to the abutment, which would be made in the same manner as the locking of the prosthesis to the replica. Any open space appearing between the prosthesis and the abutment due to differences in height between the abutment and the replica may be filled with a filling material.

In a fifth aspect of the invention there is provided a simplified method for making a master cast of a modified standard abutment using components suitable for taking impressions of both standard and of modified abutments.

Other advantages and features of the invention will appear from the following description and drawings, that are to be regarded as non-limiting examples only, in which:

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF PREFERRED EMBODIMENTS

Figure 1A:
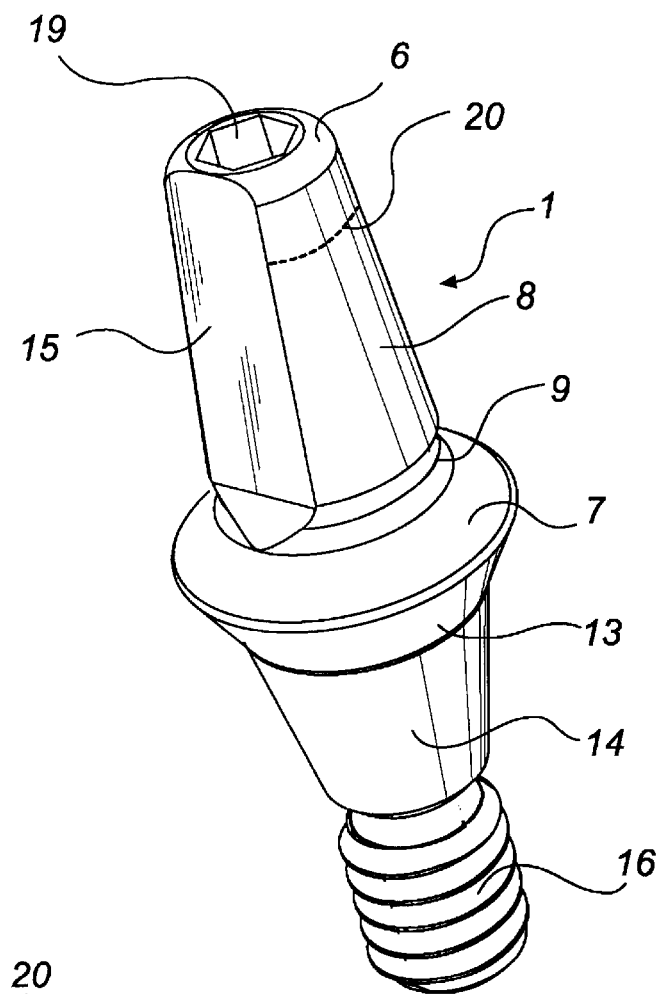
FIGS. 1a to 1e depict a first embodiment of an abutment.

FIG. 1a is a perspective view of a first embodiment of an abutment, whereas FIGS. 1b to 1e are lateral views of the same abutment as in FIG. 1a.

Figure 1B:
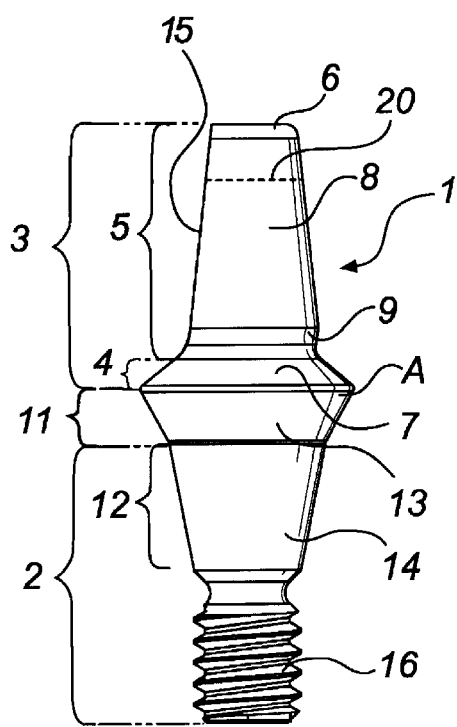

Turning first to FIGS. 1a and 1b, an abutment for connection of a dental component to an implant is depicted. The abutment comprises an implant contacting region 2 for connection to a dental implant and a component support region 3, extending coronally of said implant contacting region 2, for connection of a dental component thereto.

Typically, the abutment would be used for connection of a dental prosthesis or crown to the implant. However, during the procedure of manufacturing the final prosthesis, the abutment would be used for connecting other components to the implant, such as for example impression copings, healing caps or a temporary prosthesis. The abutment 1 may be made of a suitable material for dental components to be permanently installed in the mouth, such as for example titanium and certain ceramic materials, for example zirconium oxides.

The component contacting region 3 extends coronally from a maximum diameter A (see FIG. 1c) to a coronal end 6. The maximum diameter A of the component contacting region is in this case coinciding with the maximum diameter of the abutment as a whole.

Component engagement means 9 is provided at the component support region 3, coronally of the maximum diameter A. The component engagement means is structured and adapted for releasable engagement with a component by linear displacement of said component in relation to said abutment.

The location of the component engagement means 9 coronally of the maximum diameter A result in the attachment of the component being made where the abutment has a relatively narrow diameter, which is advantageous since it allows the components to be attached thereto to be constructed with a relatively small outer diameter. A small outer diameter makes it easier to install the component on the abutment without being hindered by adjacent teeth or having to push aside and damage the gingival tissue surrounding the abutment 1, when installed.

The component engagement means 9 is provided at a distance from said maximum diameter A being less than 50% of the distance between the maximum diameter A and the coronal end 6 of the abutment. Preferably, the distance should be less than 35%, and, as in the embodiment of FIGS. 1a to 1e, the component engagement means 9 is provided at a distance being less than 25% of the distance between the maximum diameter A and the coronal end 6 of the abutment.

The implant contacting region 3 comprises in this first embodiment a shoulder portion 4 and a post portion 5, extending coronally from said shoulder portion. The outer surface 8 of the post portion 5 is forming an angle α less than 180° with the outer surface 7 of the shoulder portion. (See FIG. 1e). The angle α formed between the outer surfaces 7, 8 of the shoulder portion 4 and the post portion 5 is preferably between 100° and 160°, more preferred 120 to 150°, most preferred 130 to 140°. In this embodiment, the angle α is 136°.

In this embodiment, the component engagement means 9 is provided at the transition between said shoulder portion 4 and post portion 5. This placement allows the major part of the post portion 5 to be modified without impairing the function of the component engagement means 9. The component engagement means 9 has the shape of a groove extending around part of the circumference of the post portion 5. The groove may be described as formed by a transition part 5' of the post portion 5 having an outer surface 8' that forms an angle δ with the outer surface of the post portion 5. The angle 6 is preferably in the range of 10 to 40°, more preferred 10 to 30° degrees, most preferred 12°. Favorably, a component may be snap locked onto the groove formed by said transition part 5'. The angle δ as defined above is suitable for forming such a snap lock having a preferred retaining force for securely retaining the component on the abutment 1 while still enabling the component to be released from said abutment 1.

As related to the shoulder portion 4, the component engagement means 9 is preferably provided at a distance from the shoulder portion 4 being less than 50%, more preferred less than 30% and, as in this embodiment, less than 20% of the distance from the shoulder portion 4 to the coronal end 6 of the abutment. A component engagement means 9 may be considered as being provided at a distance from the shoulder portion 4 being less than 50% the distance between the shoulder portion 4 and the coronal end 6 if the component engagement means 9 is still providing a component retaining function if a coronal portion of the abutment corresponding to 50% of the distance between the shoulder portion 4 and the coronal end 6 is cut off. (A corresponding definition applies to the situation where the location of the component engagement means 9 are related to the maximum diameter A.)

The post portion 5 is further provided with a rotational locking means 15 for rotational locking of a component attached to the abutment 1. In this case, the rotational locking means 15 is made out of a flat part of the outer surface 8 of the post portion 5. However, other shapes of the rotational locking means 15 may be considered. It is believed that a relatively smooth rotational lock function is preferred over more sharp and distinct locking means, since a smooth lock allows more play when installing a component on the abutment.

The coronal end 6 of the post portion is optionally provided with a polygonal blind bore 19, serving as attachment for a wrench for screwing the abutment onto an implant.

Between the component support region 3 and the implant contacting region 2 there is provided an extension region 11, serving to increase the heigh with which the abutment 1 is extending over the implant when installed thereto. When installed to an implant being flush with bone tissue, the extension region 11 would typically extend through gingival tissue.

The implant contacting region 2 comprises a coronal contact portion 12 and a threaded shaft 16. The implant contacting region 2 is thereby adapted for connection to an implant having a conical coronal opening and being provided with internal threads for attachment of an abutment 1. The conical shape of the implant contacting region 2 and the implant opening, respectively, is particularly advantageous since it may be adapted to give rise to a conical seal when the implant and the abutment are screwed together.

Figure 1C:
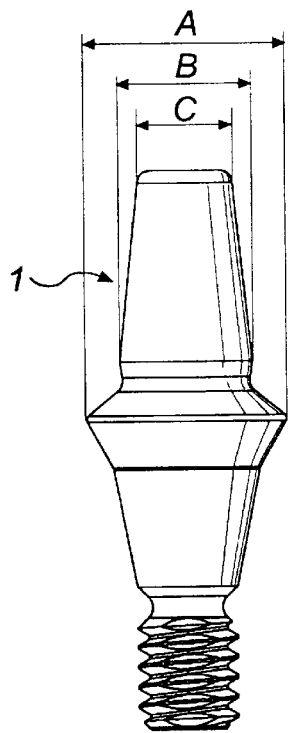
Figure 1E:
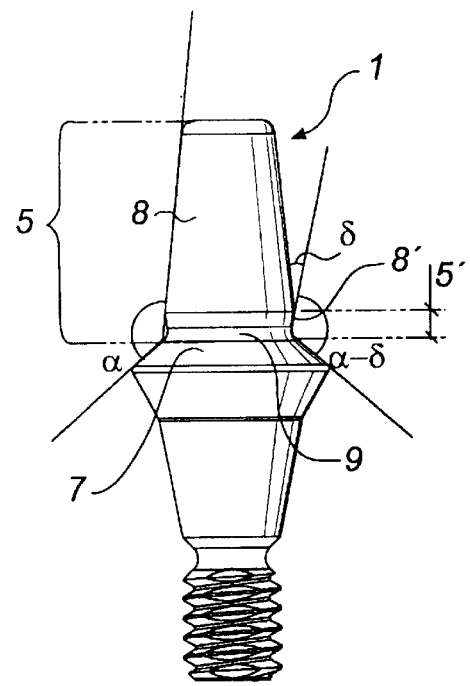
Figure 1D:
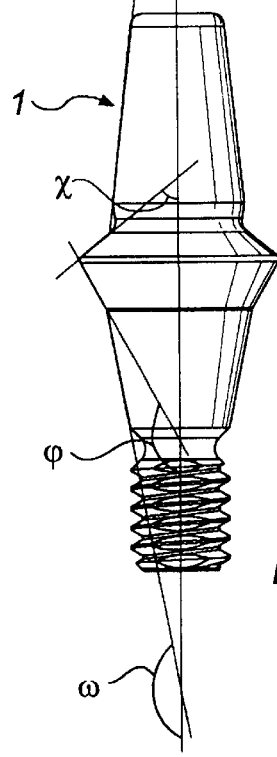

In FIG. 1d the angles formed by the outer surfaces of different portions of the abutment 1 with a longitudinal axis L of the abutment is indicated.

The outer surface 8 of the post portion 5 is tapering towards the coronal direction of the abutment. This is believed to be advantageous, since it allows more lateral play in an initial stage of attaching a component to the abutment 1, than would be the case if the outer surface 8 of the post portion 5 was parallel to the longitudinal axis L. The angle φ formed by the outer surface 8 of the post portion 5 with the longitudinal axis L is preferably less than 20°, more preferred less than 15°. In this case, the angle φ is 6°.

The above mentioned values of the angle φ are particularly suitable for providing a post portion 5 that may cooperate with a component to provide a retaining function between the post portion 5 and the component.

Returning now to the component engagement means 9 as previously described is formed by a transition part 5' of the post portion 5 having an outer surface 8' that forms an angle δ with the outer surface of the post portion 5. The angle δ may further be described in relation to the angle φ between the longitudinal axis and the outer surface 8 of the post portion, as advantageously being 2φ±10°. This particular choice of angle δ enables a component attached to the abutment to be released from said abutment by linear displacement with essentially the same force that was needed for attaching the component to said component engagement means. If the outer surface 8 of the post portion 5 in general forms an angle φ with said longitudinal axis L, the outer surface 8' of the transition part 5' of the post portion will namely form an angle φ' in relation to the longitudinal axis L, φ' being equal to φ±10°.

If using a component having an inner shape having at least some inner surfaces corresponding to the outer shape of the abutment, the force required for attaching the component onto the abutment will be dependent on the angle φ formed by the outer surface 8 of the post portion 5 with said longitudinal axis L. The force required for removing the component from the abutment will be dependent on the angle formed by the outer surface 8' of said transition portion 5' with said longitudinal axis L. When the angle δ is 2φ±10°, this angle will be φ±10°, meaning that the force required for removing said component from said abutment is essentially the same as the force required for attaching said component to said abutment 1.

The outer surface 7 of the shoulder portion 4 is likewise tapering inwardly in a coronal direction. The angle χ formed by the outer surface 7 of the shoulder portion 4 with the longitudinal axis L is preferably in the range 40 to 60°. In this case, the angle χ is 50° degrees.

The before mentioned angle α formed between the outer surface 7 of the shoulder portion 4 and the outer surface 8 of the post portion 5 would be equal to (180°+φ−χ).

The outer surface 13 of the extension region 11 may be parallel to a longitudinal axis of the abutment 1 or tapering outwardly in a coronal direction of the abutment 1. The angle φ formed by the outer surface 13 of the extension region 11 with said longitudinal axis L may advantageously be varied so as to achieve a desired maximum diameter A. Preferably, the angle φ would be 90° to 180°.

Finally, the angle ω formed by the outer surface 14 of the coronal contact portion 12 of the implant contacting region 2 of the abutment 1, is preferably 165° to 170°, in this case 169°.

Turning to FIG. 1c, the maximum diameter A of the abutment 1 is preferably in the range 3 to 7 mm, most preferred 3 to 6 mm. The maximum diameter B of the post portion 5 is in the range 2 to 5 mm. A shelf formed by the outer surface 7 of the shoulder portion 4 would in this embodiment have a width corresponding to half the difference between said maximum diameter A of the abutment and the maximum diameter B of the abutment. Preferably, this width may be in the range 0.2 to 1 mm, most preferred 0.5 mm.

The axial extension of the shoulder portion 4 may be in the range 10–40%, preferably 20% as compared to an axial extension of the entire component support region 3. The axial extension of the extension region 11 may advantageously be selected so as to achieve a desired height of the abutment. Normally, the extension region 11 would have an axial extension of about 10% to 50% of the axial extension of the component support region 3.

Optionally, the abutment 1 may be provided with one or several markings 20 indicating a level for shortening of the abutment.

Figure 2A:
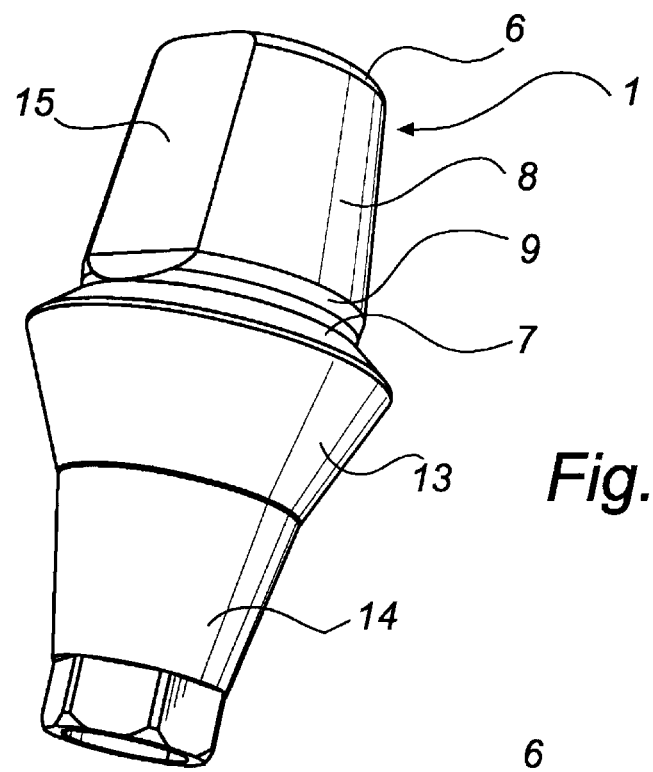
FIGS. 2a to 2b depict a second embodiment of an abutment.
Figure 2B:
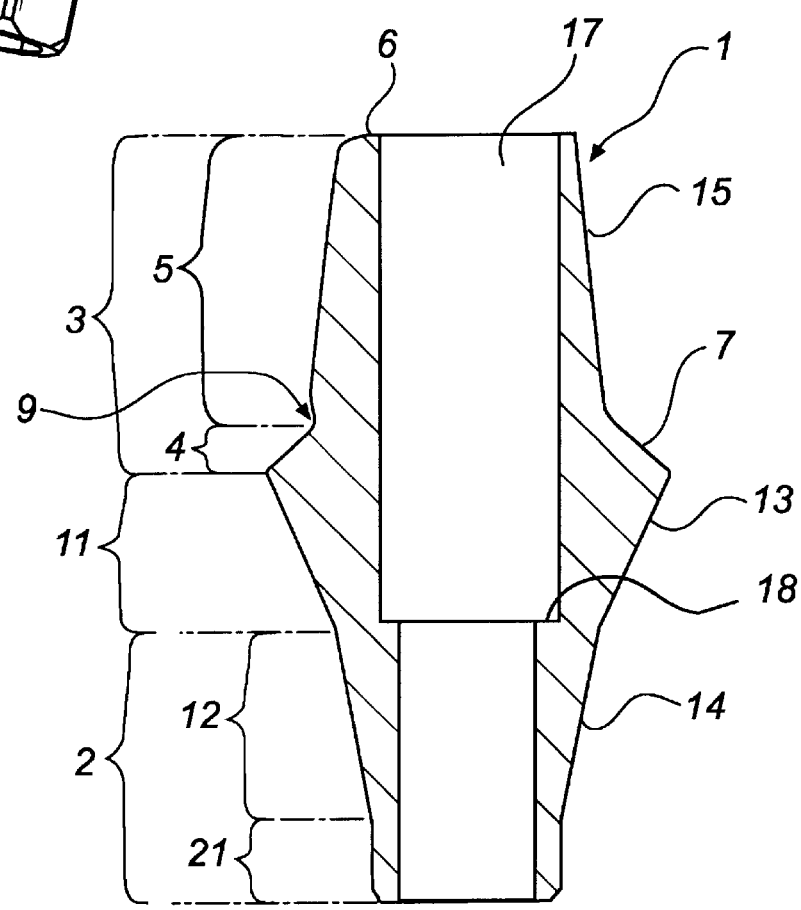

FIG. 2a is a perspective view of a second embodiment of an abutment. FIG. 2b is a sectional view of the abutment of FIG. 2a. Features corresponding to features of the above mentioned first embodiment of FIGS. 1a to 1e have been provided with the same reference numerals as used in FIGS. 1a to 1e. Only the parts of this second embodiment that differ from the first embodiment will be described below.

The second embodiment differs from the first embodiment in that the implant contacting region 2 is not provided with a threaded shaft 16. Instead, it has a hexagonal locking structure 21 for rotational lock to an implant. The abutment 1 is further provided with a through bore 17 having an internal ledge 18. A screw may be inserted in the through bore 17, seating the screw head on the ledge 18, for connection of the abutment 1 to an implant. This type of abutment is particularly useful for single-tooth restoration situations.

Figure 3:
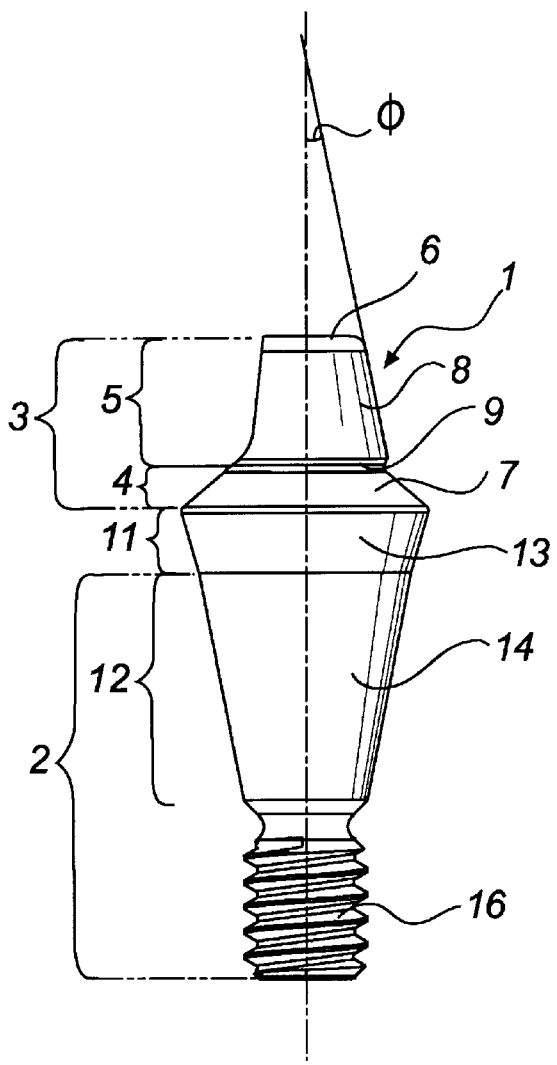
FIG. 3 depicts a third embodiment of an abutment.

FIG. 3 is a side view of a third embodiment of an abutment. Features corresponding to features of the above mentioned first embodiment of FIGS. 1a to 1e have been provided with the same reference numerals as used in FIGS. 1a to 1e. Only the parts of the third embodiment that differ from the first embodiment will be described below.

The third embodiment of the abutment differs from the first embodiment mainly in the height and shape of the post portion 5. The height of the post portion 5 is shortened as compared to the first embodiment, and constitutes approximately 75 to 80% of the axial extension of the component support region 3. (This leaving about 20 to 25% of the axial extension to the shoulder portion 4). The actual length of said post portion is about 2 mm. The angle φ formed by the outer surface 8 of the post portion 5 with the longitudinal axis L is 11°.

An advantage with using an abutment 1 with a short post portion 5 is that the abutment 1 will not need being modified very often. Instead, the prosthesis may be built on the post portion 5 in its original shape.

Figure 4:
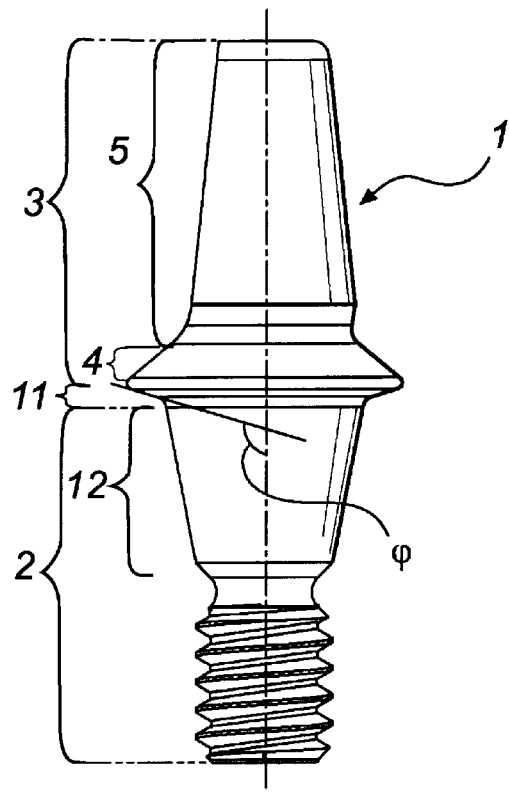
FIG. 4 depicts a fourth embodiment of an abutment.

FIG. 4 is a side view of a fourth embodiment of an abutment 1. Features corresponding to features of the above mentioned first embodiment of FIGS. 1a to 1e have been provided with the same reference numerals as used in FIGS. 1a to 1e. Only the parts that differ from the first embodiment will be described below.

The fourth embodiment differs from the first embodiment in that the extension region 11 is made very short and its outer surface 13 is forming a rather large angle φ with said longitudinal axis L.

FIGS. 5a to 5h depict an embodiment of a series of abutments of the types described in FIGS. 1a to 4. The reference numerals in the following description of FIGS. 5a to 5h may be referred to features described in FIGS. 1a to 4.

FIGS. 5a to 5h depicts a series of abutments wherein the angle α formed between the outer surface 8 of the post portion 5 and the outer surface 7 of the shoulder portion 8 is constant for all abutments in said series. Further, the longitudinal extension of a component support region 3 is constant between all abutments in said series.

Figure 5A:
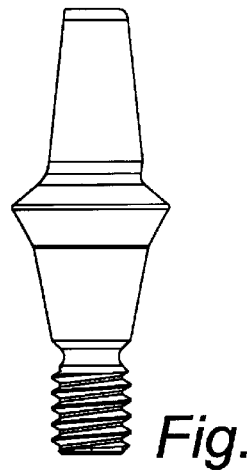
FIGS. 5a to 5h depict an embodiment of a series of abutments.
Figure 5B:
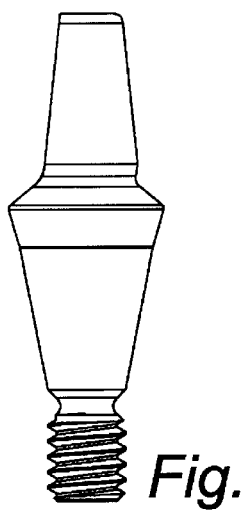
Figure 5C:
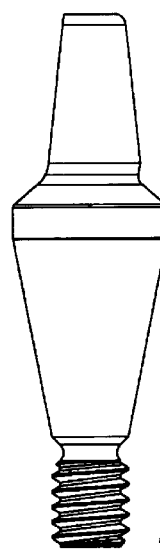
Figure 5D:
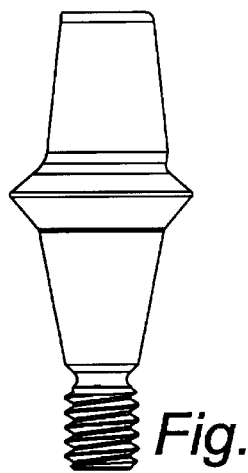
Figure 5E:
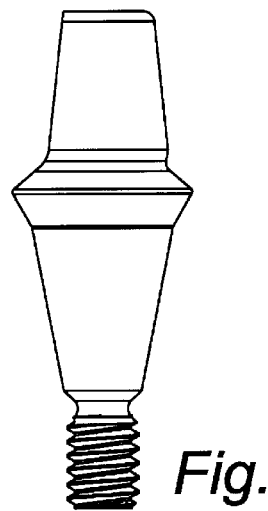
Figure 5F:
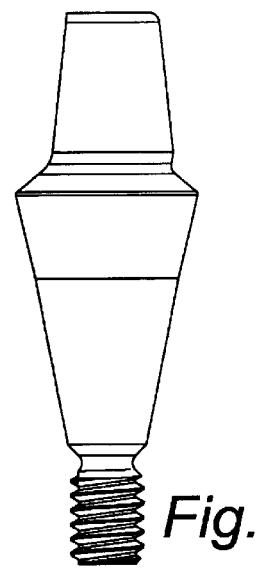
Figure 5G:
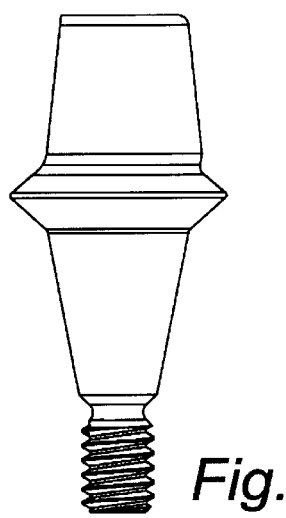
Figure 5H:
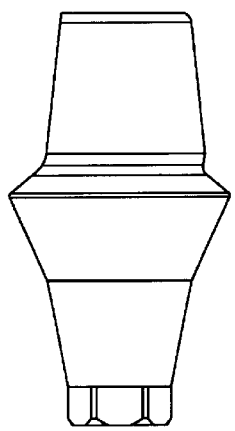

Turning to FIGS. 5a to 5c only, these three abutments further belong to a series in which the maximum diameter A is constant for all abutments in said series. Likewise, the three abutments of FIGS. 5d to 5f have a common maximum diameter, and the two abutments of FIGS. 5g to 5h have a common maximum diameter. The abutments of FIGS. 5a to 5c have a maximum diameter of 4 mm, the abutments of FIGS. 5d to f have a maximum diameter of 5 mm, and the abutments of FIGS. 5g and 5h have a maximum diameter of 6 mm.

FIGS. 5a to 5h describes a series of abutments 1 for connection of a dental component to an implant, each abutment having a longitudinal axis L and comprising an implant contacting region 2, a component support region 3 and an extension region 11 there between 3, wherein said extension region 11 presents an outer surface 13 forming an angle φ with said longitudinal axis L, said shoulder portion 4 presents an outer surface 7 tapering inwardly in a coronal direction and forming an angle χ with said longitudinal axis L, said post portion 5 extending coronally from said shoulder portion 4 and presenting an outer surface 8 tapering inwardly in a coronal direction and forming an angle φ with said longitudinal axis L being less than the angle χ formed by the outer surface 7 of the shoulder portion 4 with said longitudinal axis L, wherein, said angle χ between the outer surface 7 of the shoulder portion 4 and the longitudinal axis L and said angle φ between the outer surface 8 of the post portion 5 and the longitudinal axis L are constant in all abutments in said series, whereas the angle φ between the outer surface 13 of said extension region 11 and said longitudinal axis L varies between different abutments in said series.

Figure 6A:
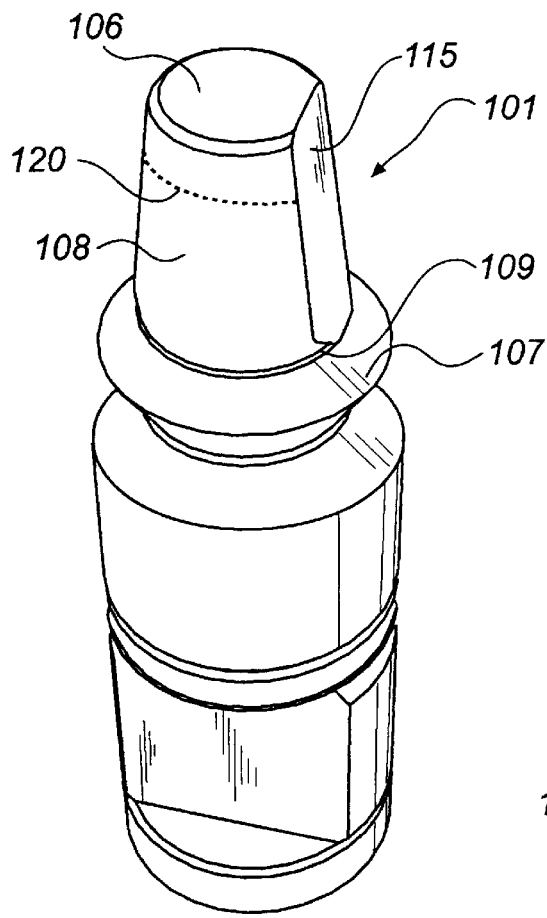
FIGS. 6a to 6b depict an embodiment of an abutment replica.
Figure 6B:
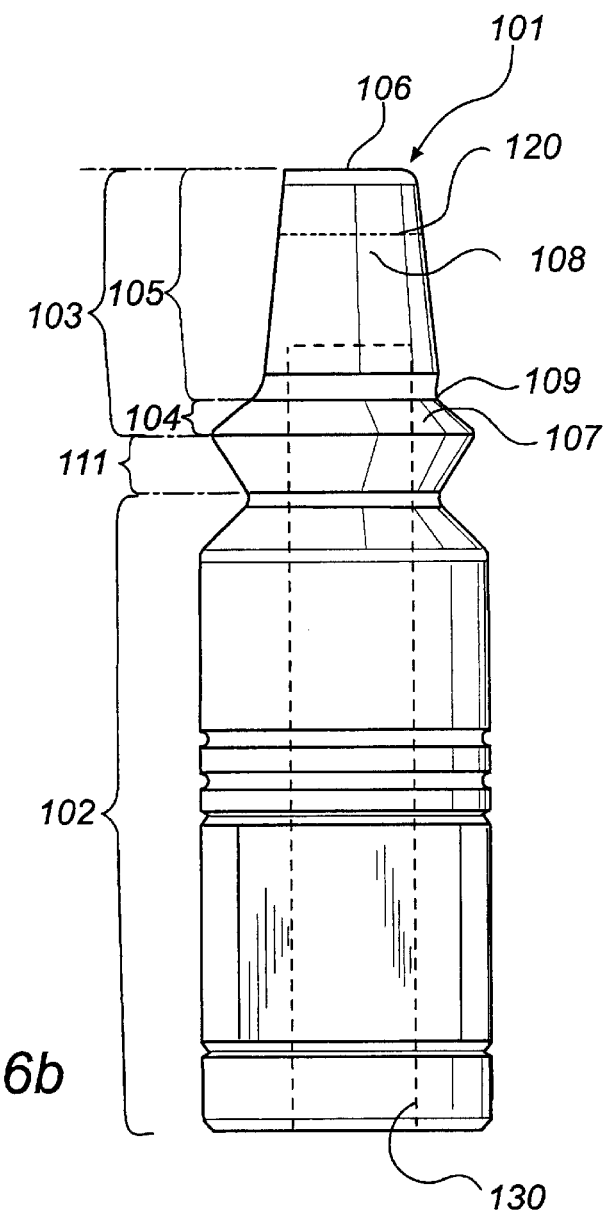

FIG. 6a is a perspective view of an embodiment of an abutment replica 101, and FIG. 6b is a side view of the same abutment replica 101.

The abutment replica 101 comprises a component support region 103, an extension region 111 and an apical region 102. The component support region 103 replicates the component support region of an abutment 1, in this case an abutment 1 of the type depicted in FIGS. 1a to 1e. Thus the component support region 103 has a shoulder portion 104 with an outer surface 107 and a post portion 105 with an outer surface 108. In addition, the post portion 105 includes a rotational locking means 115.

In particular, the abutment replica 101 is provided with component engagement means 109 replicating the component engagement means 9 of the abutment 1.

Also, the abutment replica 101 is provided with a bore 130 extending from an apical end of the apical portion 102 to a position coronally of said component engagement means 109. In this embodiment, the bore 130 is a blind bore, but one could also consider having a bore extending all the way through the replica 101.

The bore 130 becomes useful in situations where the abutment replica 101 should be used for model making of a modified standard abutment, as is described in more detail in relation to FIGS. 11a to 11h below.

In such situations, a coronal part of the post portion 105 is cut off the abutment replica 101, leaving the remaining abutment replica 101 with a through bore 130 extending therethrough. The through bore 130 may be used for pouring molding material from the apical end of the replica 101 for making a model of a modified abutment.

Thus, the abutment replica 101 is useful in pick-up impression making, regardless of whether standard or modified abutments are used.

The use of the marking 20 of the abutment 1 of FIGS. 1a to 1e, and the marking 120 on the abutment replica 101 will now be described. Preferably, there is provided a set comprising an abutment 1 having a coronal abutment end 6 and a corresponding replica 101 having a coronal replica end 106, said abutment 1 being provided with a marking for optional shortening of the abutment 1 at a first distance from the coronal abutment end 6, wherein said replica 101 is provided with a marking at a second distance from the coronal replica end 106 being equal to or slightly less than said first distance.

Such a set provides an alternative to other modification of the abutment. In case only a shortening of the abutment 1 is desired, the dental technician may shorten the abutment 1 at the marking 20. The replica 101 is provided with a corresponding marking 120 at approximately the same height as the marking of the abutment 1. Thus, the dental technician need not use specific impression techniques for capturing the modified shape of the abutment 1 when shortened, but can instead use standard techniques only to capture the location of the abutment 1. When making a master cast model, the replica 101 is shortened to the same extent as were the abutment 1, and will thus faithfully replicate the situation in the mouth.

Since it is difficult to cut off the abutment 1 and the replica 101 exactly at the marking, the marking of the replica 101 may advantageously be made at a distance from the replica end 106 being slightly less than the corresponding distance on the abutment 1. This is to provide a small margin for the dental technician when cutting of the components, without risking that the abutment replica 101 turns out to be shorter than the abutment 1.

The replica 101 and abutment 1 may each be provided with several markings.

Figure 7A:
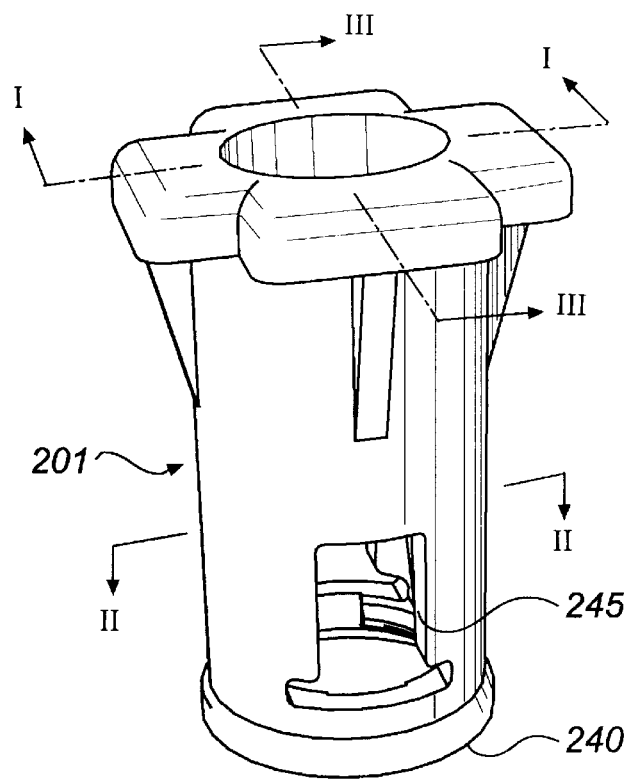
FIGS. 7a to 7f depict an embodiment of an impression coping.
Figure 7B:
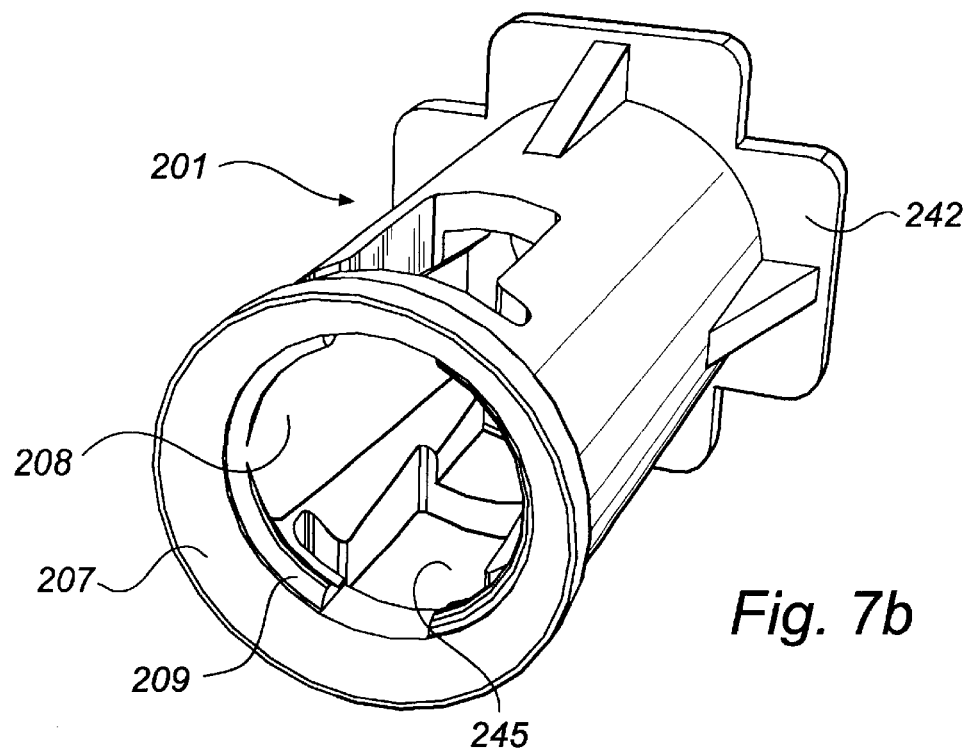
Figure 7C:
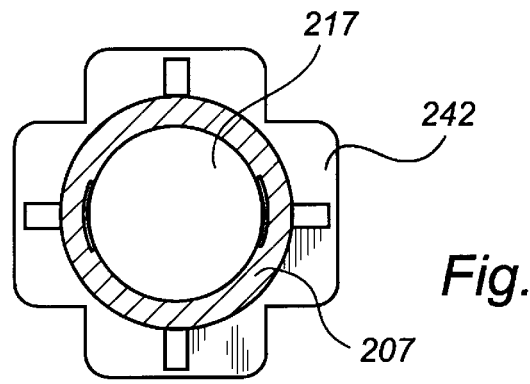
Figure 7D:
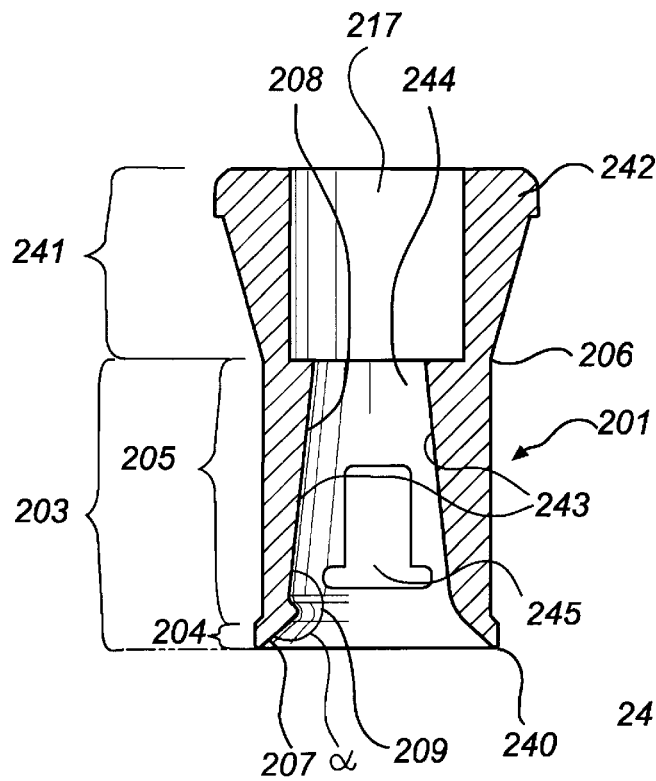
Figure 7E:
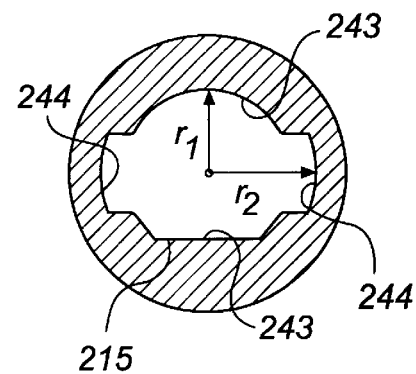
Figure 7F:
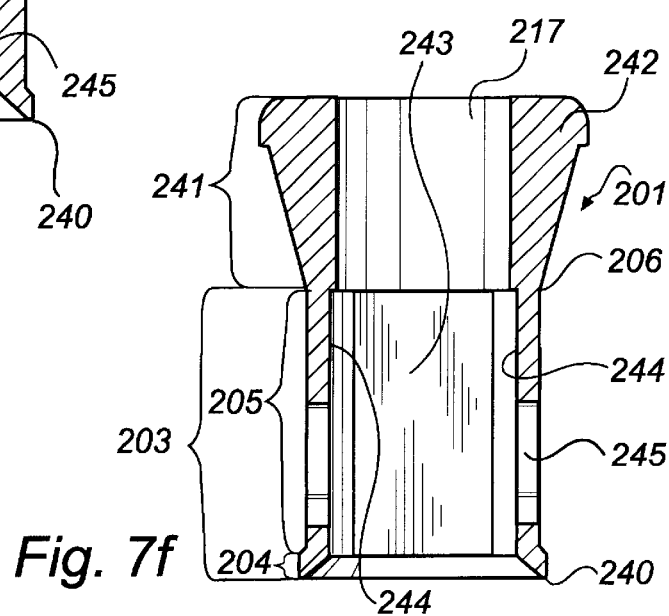

FIGS. 7a and 7b are perspective views of an embodiment of an impression coping for pick up impression making of a dental abutment attached to a dental implant. FIG. 7c is a bottom view of the same impression coping, FIG. 7d is a sectional view seen from the plane I—I in FIG. 7a, FIG. 7e is a sectional view seen from the plane II—II in FIG. 7a, and FIG. 7f is a sectional view from the plane III—III in FIG. 7a.

The impression coping as described in FIGS. 7a to 7f comprises an abutment surrounding region 203 for seating on an abutment 1. The abutment surrounding region 203 has a coronal end 206 and an apical end 240, and is provided with an inner wall 207, 208.

In this embodiment, the abutment surrounding region 203 comprises a shoulder contacting portion 204 having an inner wall 207 and a post surrounding portion 205 having an inner wall 208. The shoulder contacting portion 204 is intended to be seated on a shoulder portion of a corresponding abutment, whereas the post surrounding portion 205 will surround a post portion of said abutment.

On the inner wall 208 of the post surrounding portion 205, right at the transition between the post surrounding portion 205 and the shoulder contacting portion 204, abutment engagement means 209 are provided for releasable engagement with an abutment by linear displacement of said impression coping in relation to said abutment.

Said abutment engagement means 209 is provided closer to the apical end 240 of the abutment contacting portion 203 than to the coronal end 206. Preferably, the distance between said apical end 240 and the abutment engagement means 209 is less than 50%, more preferred less than 35%, most preferred less than 25% the distance between the apical end 240 and the coronal end 206 of the abutment surrounding region 203.

As related to the shoulder contacting portion 204, a distance between said shoulder contacting portion 204 and the abutment engagement means 209 is preferably less than 50% the distance between the shoulder contacting portion 204 and the coronal end 206 of the abutment surrounding region 203, more preferred less than 30%, most preferred less than 20%.

In this embodiment, the abutment engagement means 109 comprises a rib extending around part of the inner circumference of the inner wall 208 of the post surrounding portion 205. The rib is interrupted by the provision of flat surface functioning as a rotational lock 215 extending on the inner wall 208 of the post portion 205. It is further interrupted where space forming surfaces 244 are provided, said surfaces 244 being described further below.

The rib functions as a snap lock means when cooperating with a corresponding groove of an engagement means 9 on an abutment 1, realisably locking the impression coping 201 in an axial direction on the abutment 1.

The inner wall 208 of the post contacting region 205 comprises surface regions having different purposes. A first surface region is an abutment contact surface 243 for contact with the abutment 1 when seated. A second surface region is a space forming surface 244, that is spaced apart from the abutment 1 when seated, forming an open space between the abutment 1 and the space forming surface 244.

The abutment contact surface 243 serves to stabilise the impression coping 201 when seated on an abutment 1, and to ensure that the impression coping 201 is correctly positioned.

The space forming surface 244 serves to provide an open space between the abutment 1 and the inner wall 208 of the impression coping 201. This is particularly useful when taking an impression of a modified standard abutment, as is described in relation to FIGS. 11a to 11h below.

In a transversal section of the abutment surrounding region 203, a distance r1 from a longitudinal axis L of the impression coping 201 to an abutment contact surface 243 is shorter then a distance r2 from said longitudinal axis L to a space forming surface 244. This distinction is possible since abutments 1 are usually symmetrical or close to symmetrical around a longitudinal axis, why an asymmetrical inner surface of the impression coping 201 generally means that spaces between the impression coping 201 inner surface and the abutment 1 will be provided when the impression coping 201 is attached to the abutment 1.

Put another way, the space forming surface 244 is a surface deviating from an outer contour of a corresponding abutment, while the abutment contact surface 243 is a surface following said outer contour.

Preferably, said space forming surface 244 may be provided with a vent 245 for passage of air from said space formed between the space forming surface 244 and a corresponding abutment, when the impression coping 201 is seated on said abutment. When impression material is introduced into at least part of said space, air may flow from said space out through the vent 245, whereby air bubbles are avoided and proper filling of the impression coping is ensured.

In the embodiment of FIGS. 7a to 7f, the vent 245 is an opening in the wall of said impression coping. The vent may also be provided by for example a perforation.

Advantageously, the space forming surfaces 244 are extending longitudinally along the inner wall 208 of the post surrounding portion. As such they may form ducts for air and sometimes impression material to flow through. Vents 245 may be provided at the apical end of such ducts, being the most advantageous location for ensuring that air is let out, provided the impression material is filled from a coronal end of the impression coping 201. Also, vents 245 may be dispersed over the space forming surfaces.

The wording of the terms "space forming surface" 244 and "abutment contact surface" 243 is related to when the impression coping 201 is seated on an unmodified abutment. However, when taking an impression of a modified abutment, all of the abutment contact surface 243 will probably not be in contact with the modified abutment. At least a portion of the abutment contact surface 243 will most likely not contact the customised abutment, due to the modified shape thereof. In this case a composite space is formed between the abutment and the inner wall of the impression coping 201, said composite space being composed by a space between the abutment contact surface 243 and the modified abutment and a space between said space forming surface 244 and said modified abutment. Impression material may be introduced into the impression coping 201 and into the composite space formed between said impression coping 201 and the modified abutment. Thus, when removed from the abutment, the impression material together with the impression coping will form an empty space having an inner "modified" shape corresponding to the shape of the modified abutment, said inner shape being subsequently used for molding a model of said modified abutment.

When the impression material is introduced into said composite space, air may flow through the space formed between said space forming surface 244 and said abutment out through the vent 245, whereby air bubbles are avoided and proper filling of the impression coping is ensured. The space forming surface 244 thus provides an air duct for air evacuation from said composite space.

Naturally, the abutment may alternatively be modified such that all of the abutment contact surface is still in contact with the modified abutment, and the composite space is related only to the space forming surfaces.

The abutment contact surfaces 243 is tapering inwardly in a coronal direction, preferably forming an angle less than 20°, more preferred less than 15° with a longitudinal axis. In this case, said angle is 6°. Further, the abutment contact surfaces form an angle with the shoulder contacting portion 204, said angle being larger than 180°, preferably 220 to 230°.

The impression coping 201 is further provided with a prolongation region 241 being provided coronally of the abutment surrounding region 203. The prolongation region 241 serves to provide a larger area for the impression material to attach to the impression coping 201. Further, it facilitates handling of the impression coping 201. For better retention of the impression material, the prolongation region 241 is provided with laterally extending retention elements 242.

The impression coping may preferably be made of a plastic material. Such a plastic material may be selected so as to provide sufficient elasticity to allow formation of a snap lock means, but not being easily deformable so that the stable transfer of location of an abutment during impression making is not impaired.

Figure 8A:
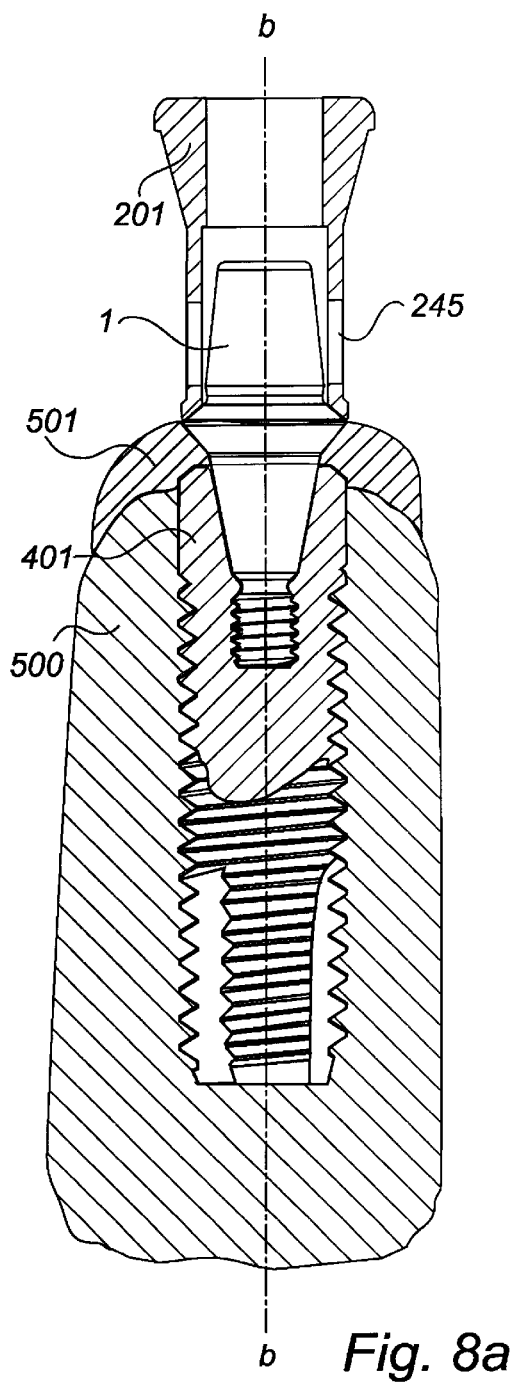
FIGS. 8a to 8b depict an embodiment of an abutment as attached to a dental implant, with an embodiment of an impression coping attached to said abutment.
Figure 8B:
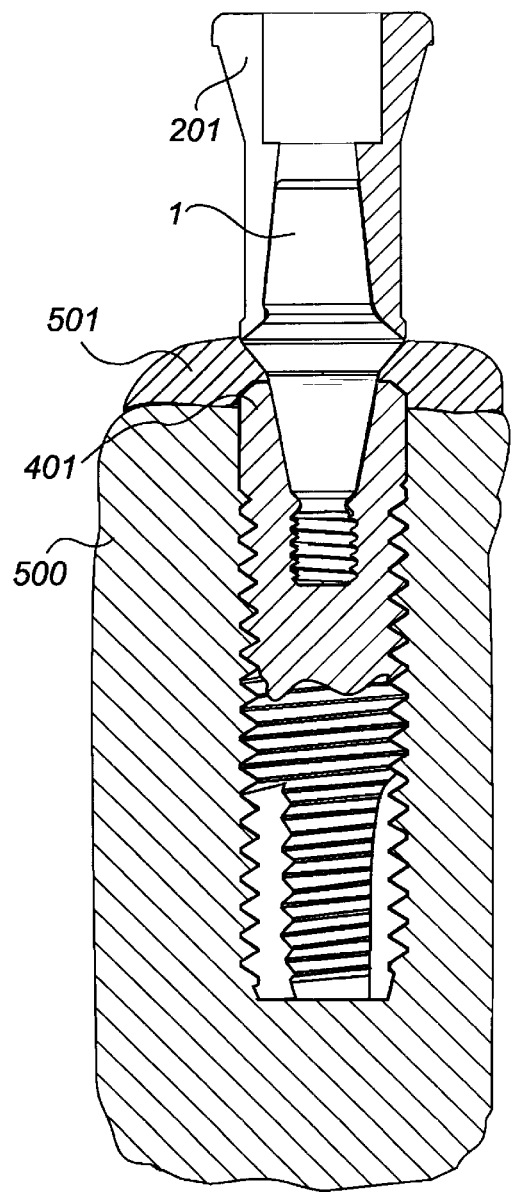

In FIGS. 8a and 8b an abutment 1 is shown as attached to a dental implant 401 implanted in bone tissue 500. An impression coping 201 is connected to the abutment 1. Both FIG. 8a and FIG. 8b are cross-sectional views, FIG. 8b being taken through the plane b—b in FIG. 8a.

The abutment 1 is of the type described in FIGS. 1a to 1e, and the impression coping 201 of the type described FIGS. 7a to 7f. The reference numerals used in the descriptions of the abutment 1 and the impression coping 201 will be used in the following, although they are not set out in FIGS. 8a and 8b for lack of space.

The abutment 1 is connected to the dental implant 401 via the implant contacting region 2 of the abutment. The threaded shaft 16 is threaded into internal threads of a coronal bore of the implant. The coronal contact portion 12 of the implant contacting region 2 is in sealing contact with a conical portion of said coronal bore of the implant 401.

The extension region 11 of the abutment is extending from implant coronal end through the gingival tissue 501. The outer diameter of the abutment is increasing from the implant contacting region 2 to a maximum diameter A at the coronal end of the extension region 11.

The component support region 3 with the shoulder portion 4 and the post portion 5 is extending above the gingival tissue 501. The component engagement means 9 is provided at the transition between the shoulder portion 4 and the post portion 5, thus coronally of both the maximum diameter A of the abutment 1, and of the shoulder portion 4.

The impression coping 201 is realisably locked to the component engagement means 9 of the abutment 1 by its own abutment engagement means 209. As seen in FIGS. 8a and 8b, the maximum diameter of the impression coping 201 is about as large as the maximum diameter A of the abutment 1. The impression coping 201 is thus easily connectable to the abutment 1 without risk of damaging the gingival tissue surrounding the abutment. This would also be the case if the gingival tissue were somewhat thicker, extending further coronally on the abutment.

In FIG. 8a it is seen that the space forming surfaces 244 of the impression coping 201 is spaced from the abutment 1. The spaces thus provided form ducts extending from the coronal end of the through passage 217 of the impression coping 201 along the side of the abutment and to the vents 245. In FIG. 8b, the abutment contact surfaces 243 is seen to contact the abutment 1, providing support and guidance for said impression coping 201.

Figure 9A:
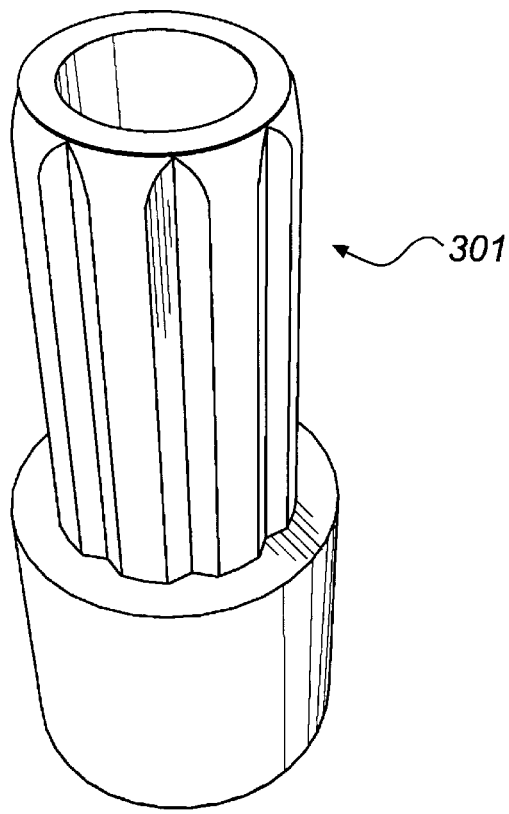
FIGS. 9a to 9b depict an embodiment of an abutment carrier.
Figure 9B:
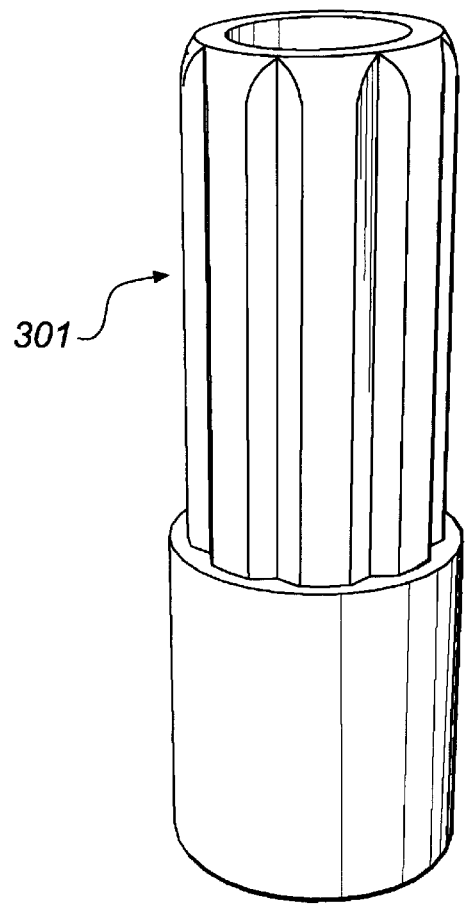

FIGS. 9a to 9b are perspective views of another component that may be connected to an abutment as shown in FIGS. 1a to 1e. The component is an abutment carrier 301, having an apical abutment contact portion and a coronal extension portion having a ribbed outer surface to facilitate gripping of the component. The abutment carrier 301 may be attached to the abutment for facilitating handling and attachment of the abutment to an implanted fixture.

Figure 10A:
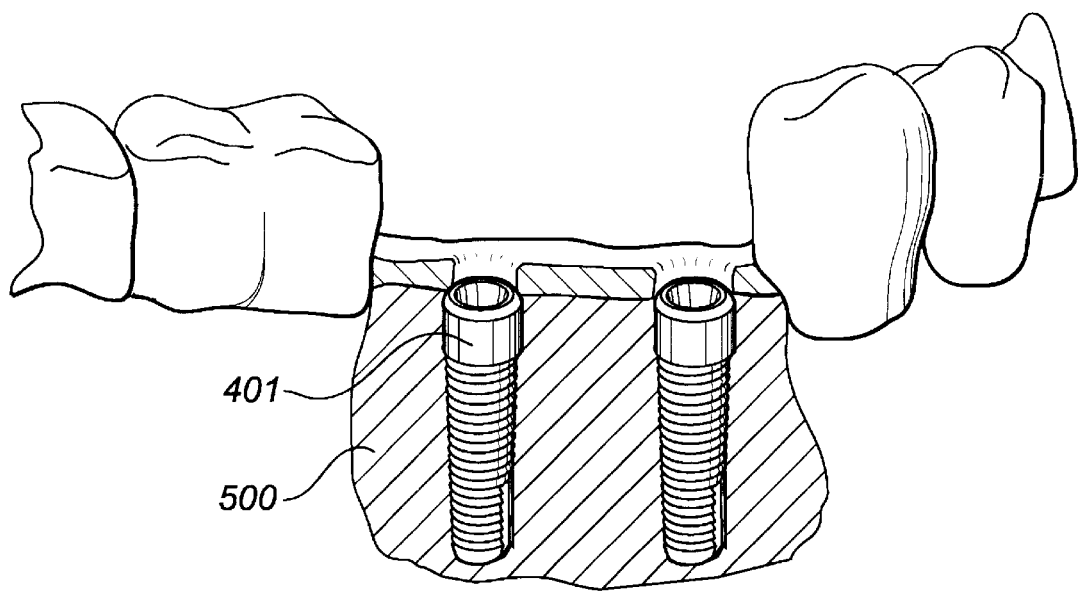
FIGS. 10a to 10h describe a method for pick up impression making of a standard abutment.
Figure 10B:
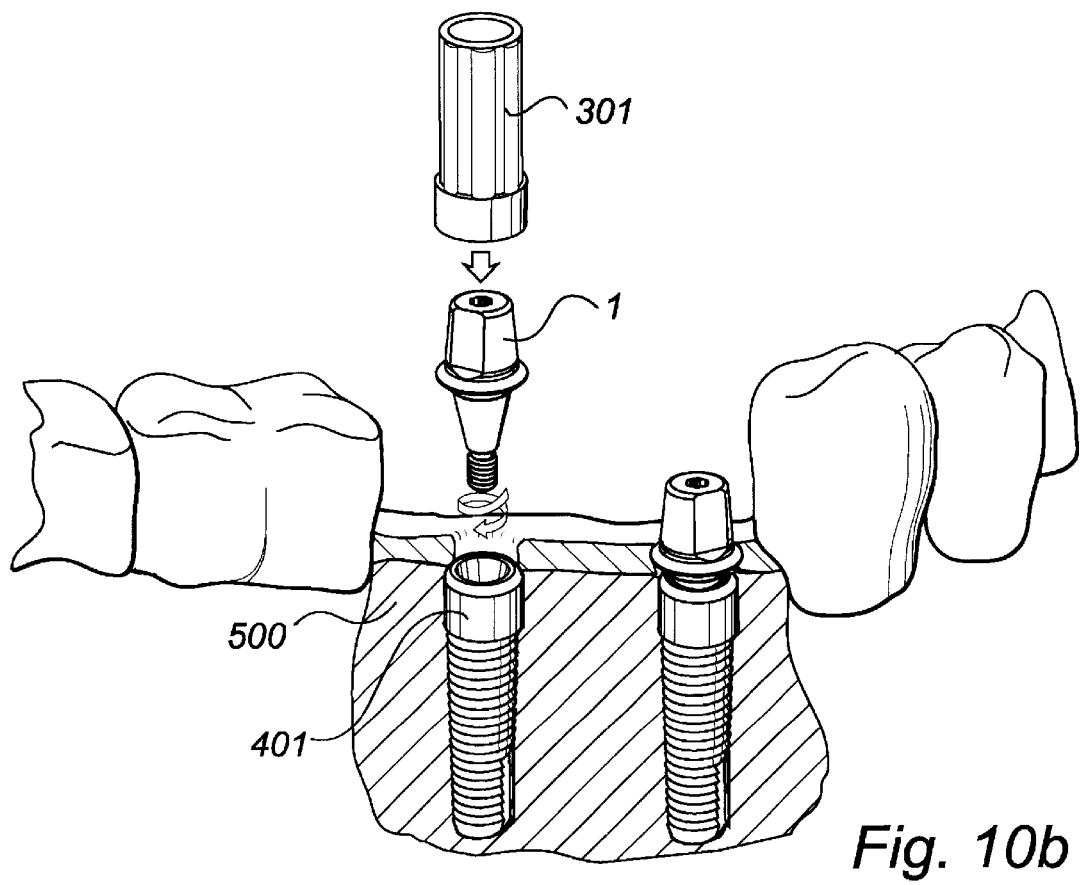

FIGS. 10a to 10b describes pick-up impression making and model forming when using a standard abutment 1.

In FIG. 10a, two dental implants 401 are shown as implanted flush with bone tissue 500 at an implantation site between adjacent teeth.

In FIG. 10b, it is illustrated how an abutment 1 is screwed into each of the implants 401 using an abutment carrier 301. The abutment 1 is attached to the carrier 301 before being brought to the implantation site. The dental surgeon initially screws the abutment 1 into the implant 401 holding the carrier 301. Thereafter, the carrier 301 is removed, and the abutment 1 may optionally be further tightened to the implant 401 using a wrench.

Figure 10C:
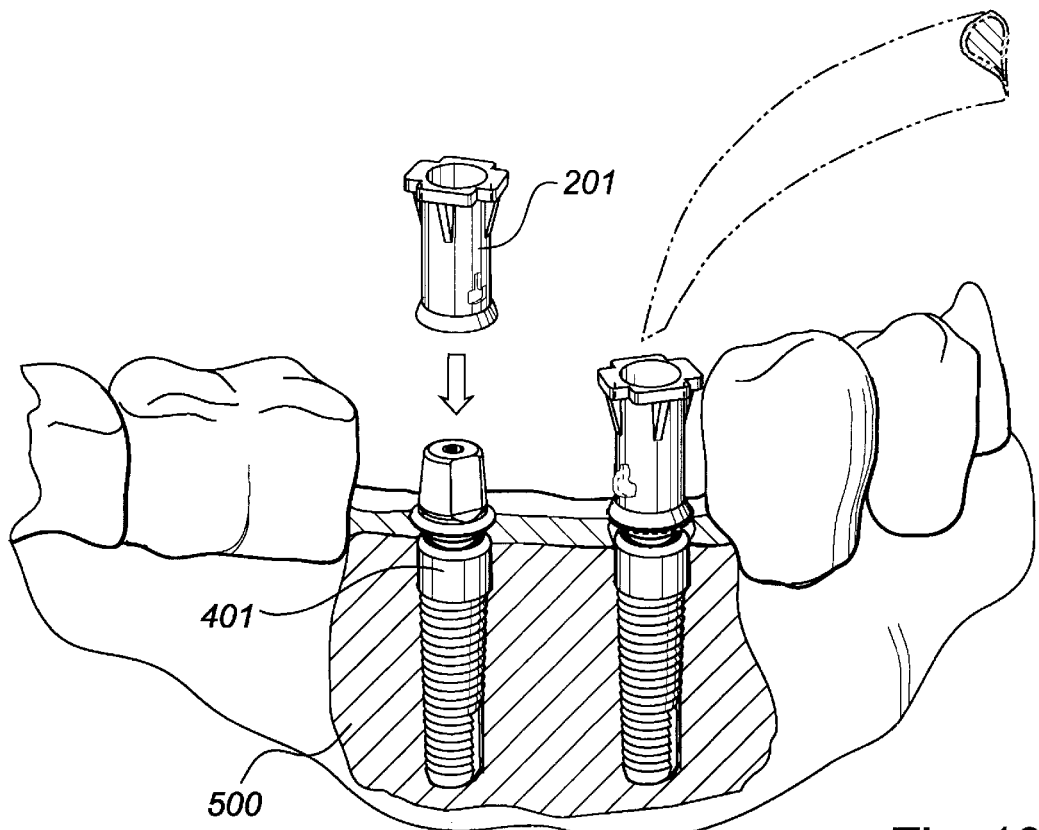

In FIG. 10c, it is illustrated how impression copings 201 are attached onto the abutments 1 using the component engagement means 9 of the abutment 1 and the abutment engagement means 209 of the impression coping 201. Optionally, impression material may be introduced into the impression coping 201. However, since a standard abutment 1 is used, this is not necessary.

Figure 10D:
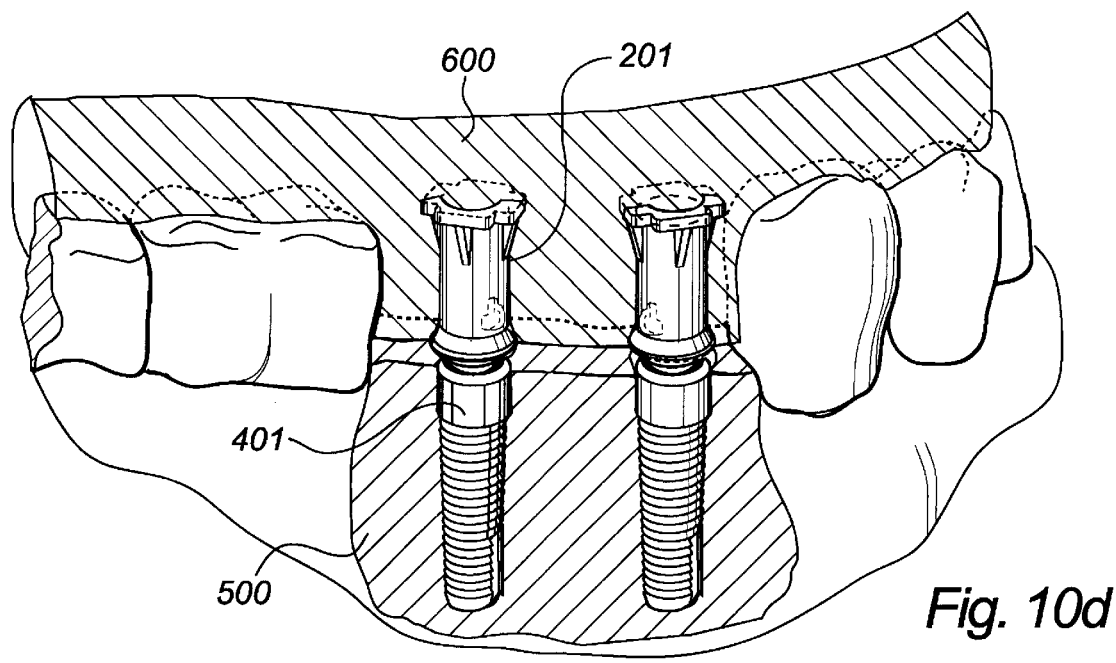

In FIG. 10d, impression material 600 has been applied, embedding the impression copings 201 in the impression material 600. The impression material 600 is let to harden so as to mimic the shape of the teeth adjacent the impression site and attach to the impression copings 201.

Figure 10E:
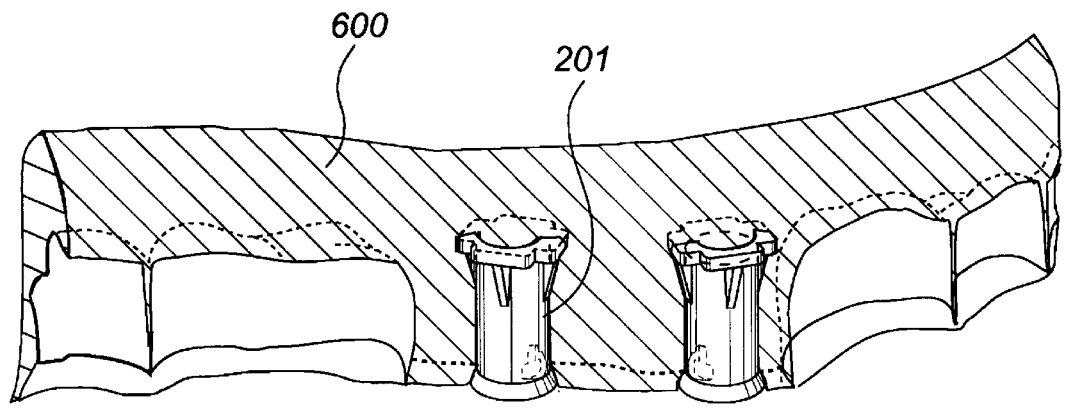

In FIG. 10e, the impression material 600 has been removed from the implantation site, bringing the impression copings 201 along embedded in the material 600.

Figure 10F:
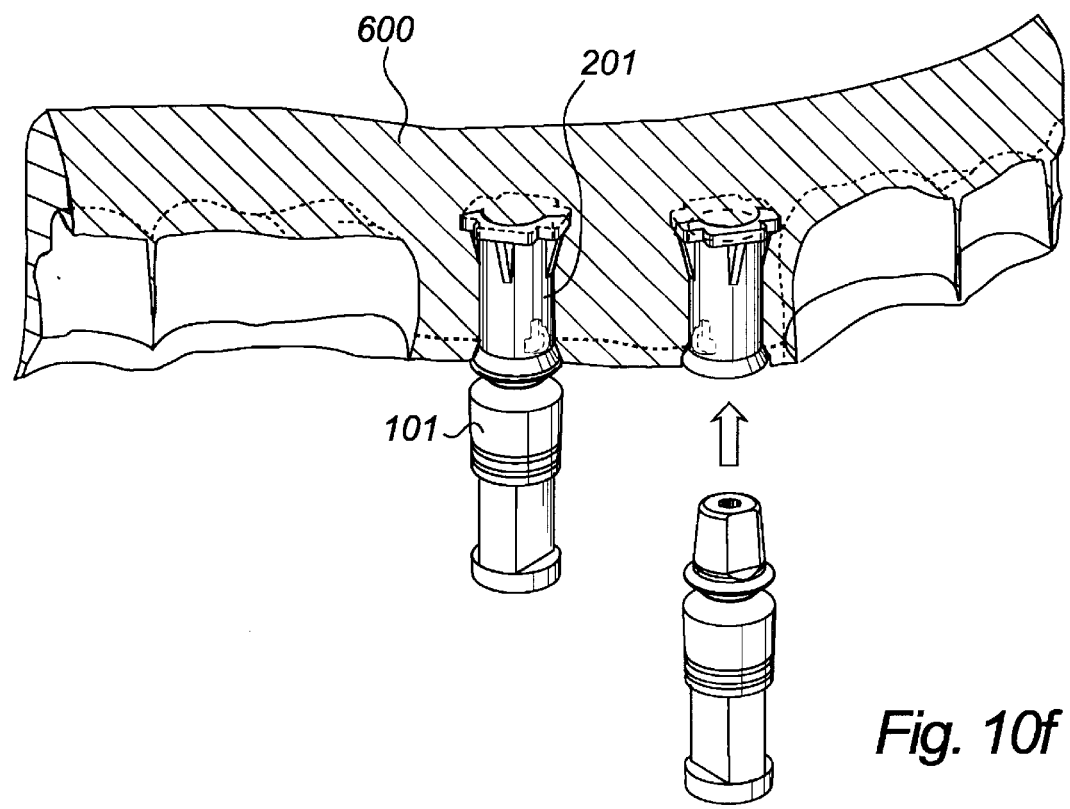

In FIG. 10f it is depicted how standard abutment replicas 101 are introduced into the impression copings 201 attached in the impression material. Due to engagement means and rotational locking means on the abutment replicas 101 and impression copings 201, respectively, the abutment replicas 101 are placed in the impression copings 201 in a position corresponding to the initial position of the abutments 1 in the impression copings 201.

Figure 10G:
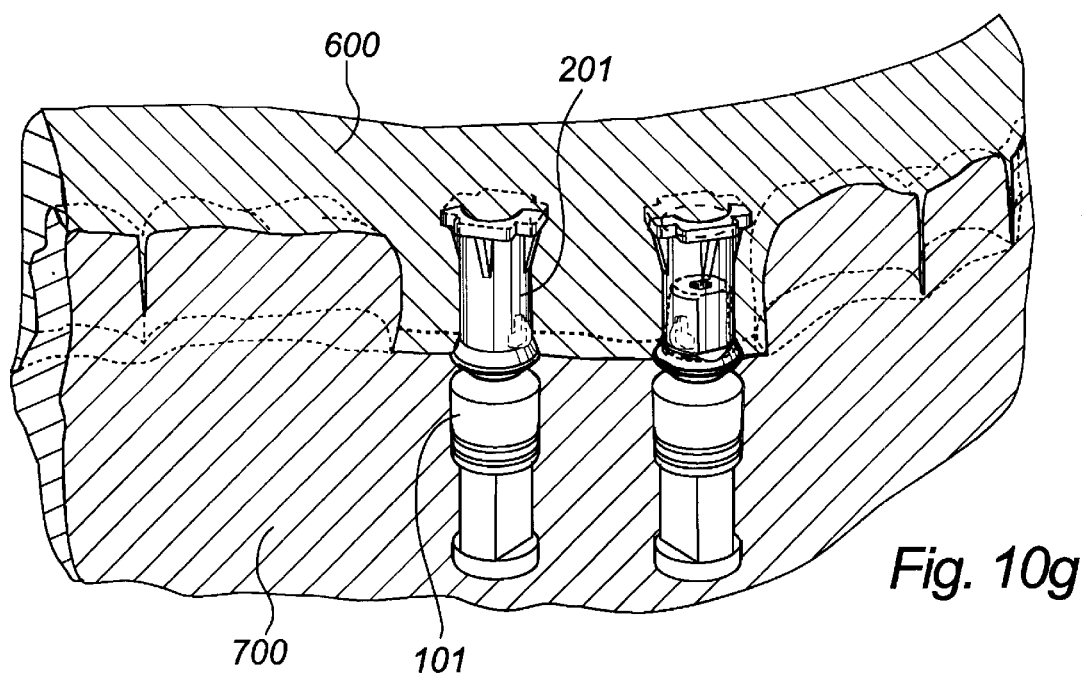

In FIG. 10g, mold material 700 has been applied to the impression material 600.

Figure 10H:
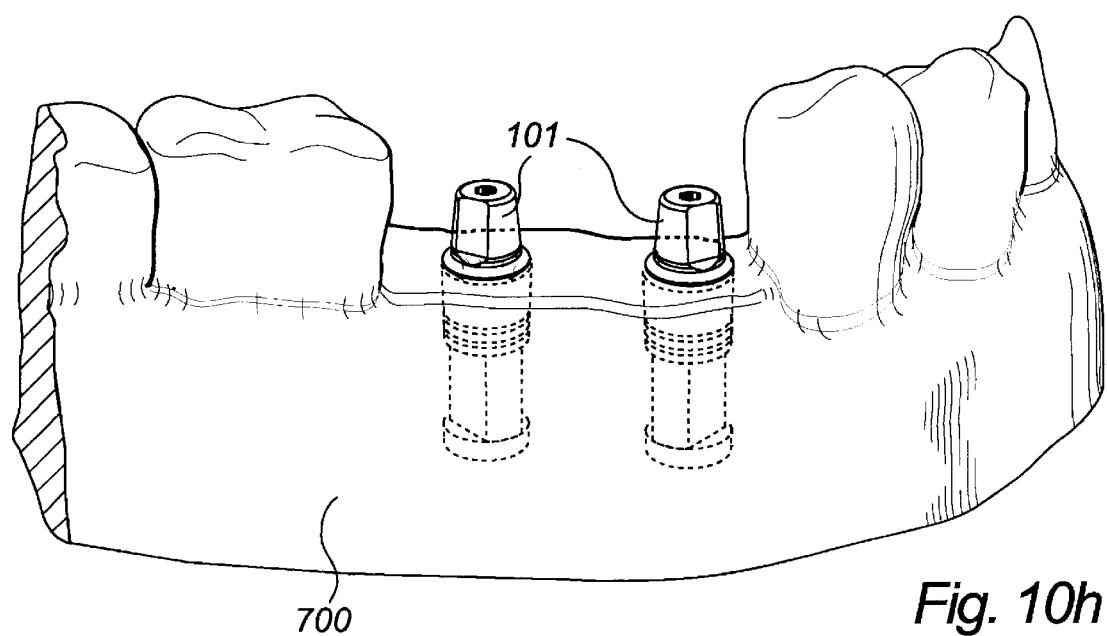

Finally, in FIG. 10h, the impression material 600 and the impression copings 201 have been removed. The molding material 700 now form a model of the implantation site with the adjacent teeth, and with the abutment replicas 101 corresponding to the abutments 1 at the actual implantation site. Using this model, a proper prosthesis or crown may be manufactured and adjusted, for later installation on the proper abutments 1 at the installation site.

FIGS. 11a to 11h describe pick-up impression making and model forming when using a modified abutment 1.

Figure 11A:
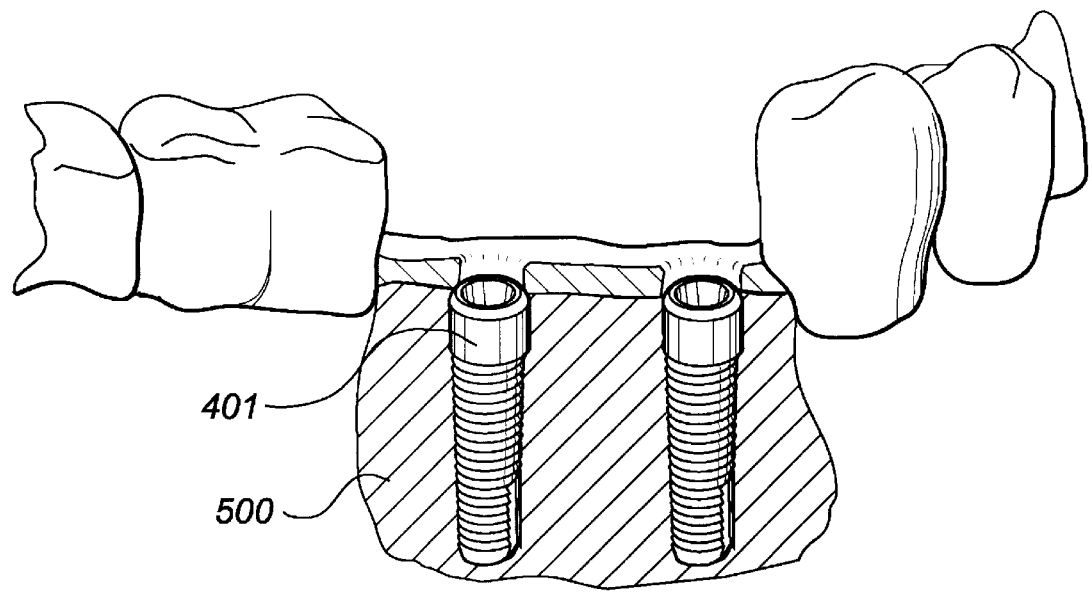
FIGS. 11a to 11h describe a method for pick up impression making of a modified standard abutment.
Figure 11:
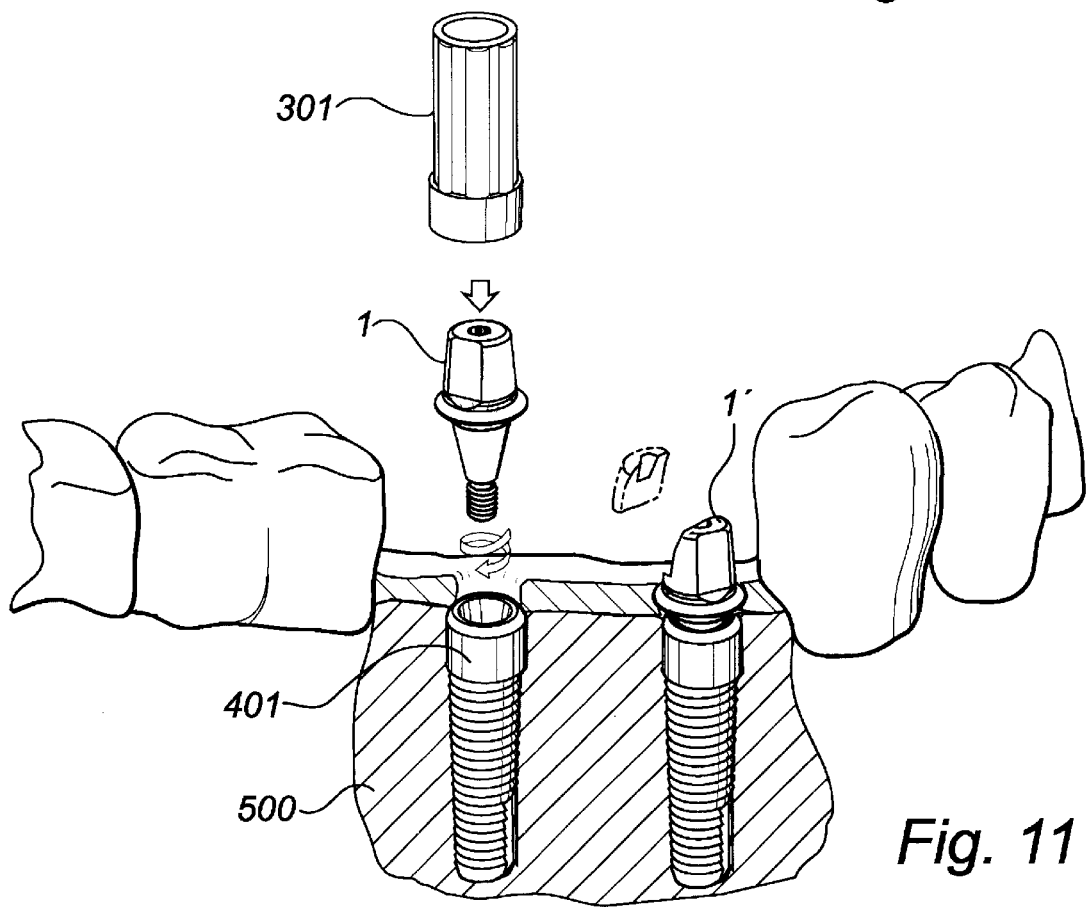

In FIG. 11a, two dental implants 401 are shown as implanted flush with bone tissue 500 at an implantation site between adjacent teeth.

In FIG. 11b, it is illustrated how abutments 1 are screwed into the implants 401 using abutment carriers 301. The abutment 1 is attached to the carrier 301 before being brought to the implantation site. The dental surgeon initially screws the abutment 1 into the implant 401 holding the carrier 301. Thereafter, the carrier 301 is removed, and the abutment 1 may optionally be further tightened to the implant 401 by using a wrench.

Thereafter, the standard abutments 1 are modified for example as shown by removing a part of the coronal portion of the abutment 1. The remaining portion is a modified abutment 1'.

Figure 11C:
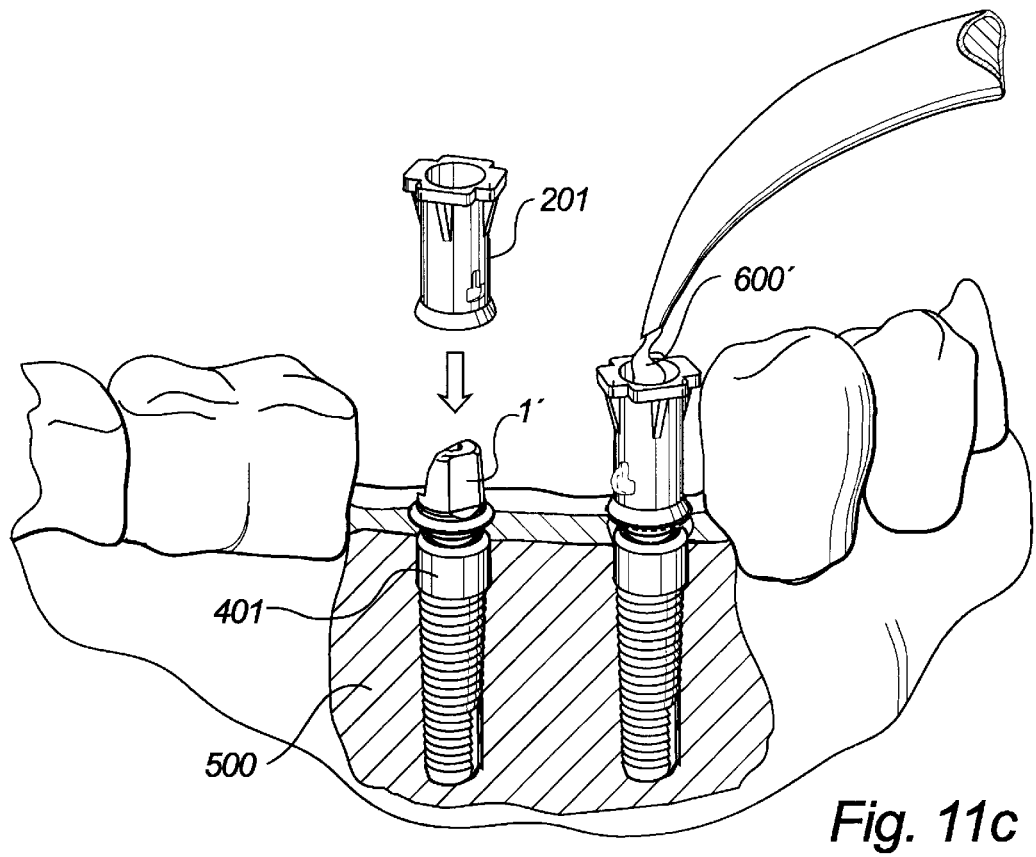

In FIG. 11c, it is illustrated how impression copings 201 are attached onto the modified abutments 1' using the component engagement means of the modified abutments 1' and the abutment engagement means of the impression copings 201, respectively. Since the abutments 1' are modified, it is necessary to introduce impression material 600' into the impression copings 201. The impression material 600' may advantageously be introduced through the coronal end of the through passage of the coping. When introducing impression material 600' through the coronal end of the through passage, air may flow through the spaces formed by the space forming surfaces 244 of the impression coping 201 and out of the vents 245, whereby air bubbles or inadequate filling of the impression coping 201 is avoided. If properly introduced, the impression material 600' together with part of the abutment contact surfaces 243 of the impression coping 201 will form an open space corresponding to the shape of the modified abutment 1'.

Figure 11D:
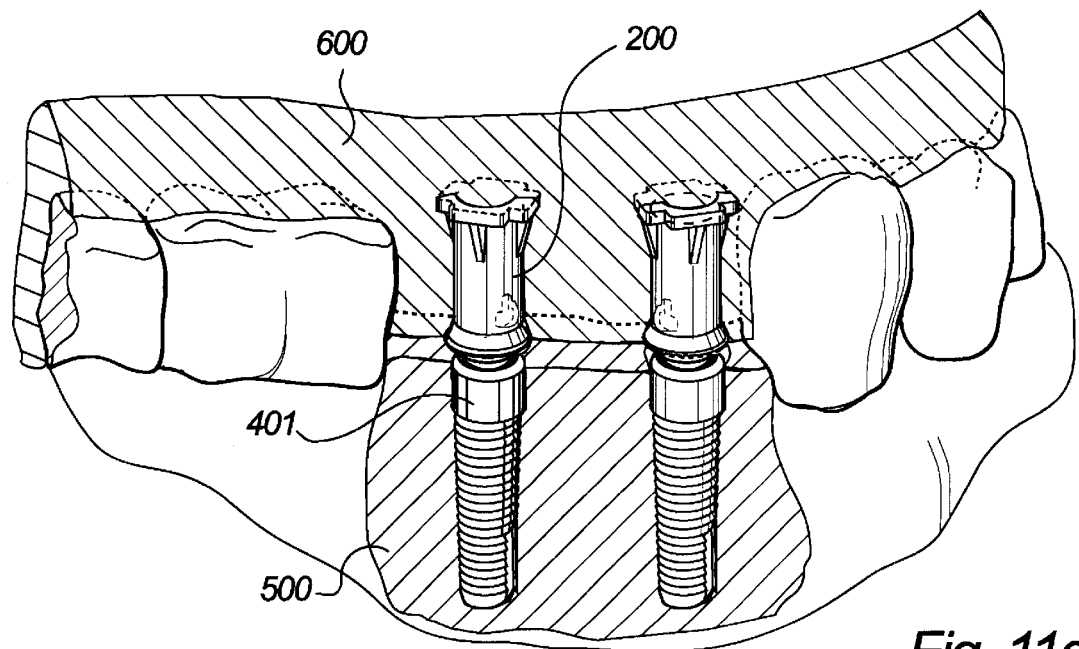
Figure 11:
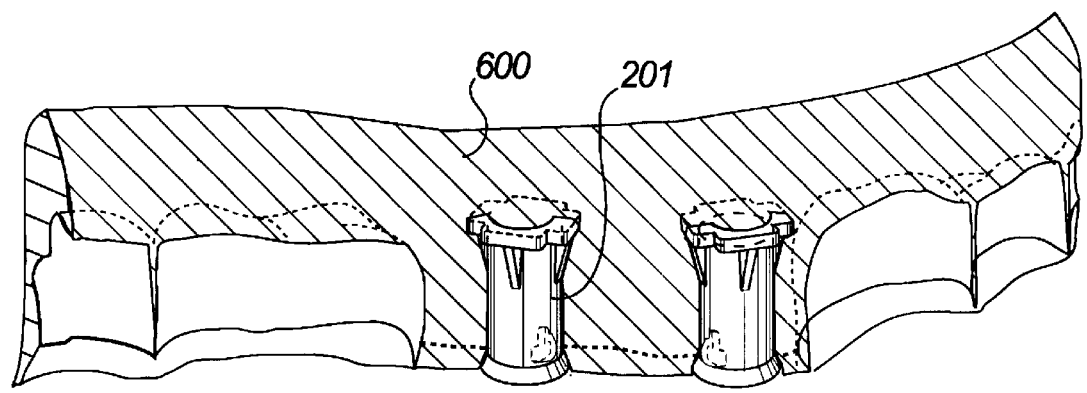

In FIG. 11d, impression material 600 has been applied, embedding the impression copings 201. The impression material 600 is let to harden so as to mimic the shape of the teeth adjacent the impression site and attach to the impression copings 201.

In FIG. 11e, the impression material 600 has been removed from the implantation site, bringing the impression copings 201 along.

Figure 11F:
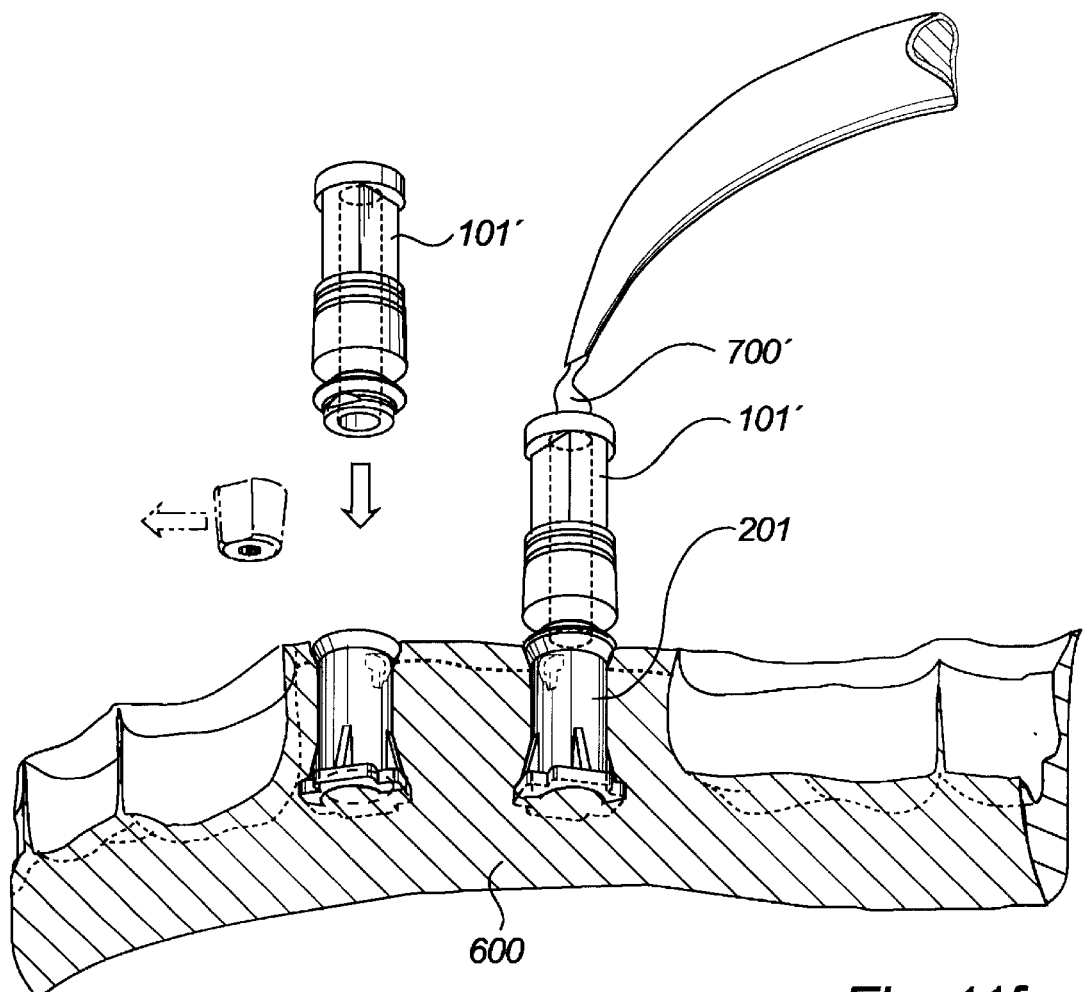

In FIG. 11f it is depicted how a coronal portion is cut off a standard abutment replica 101, so as to reveal a bore passing through the remaining part of the replica 101'. The remaining part is referred to as a cut-off replica 101'. Cut-off replicas 101' are introduced into the impression copings 201 embedded in the impression material using component engagement means 109. Thereafter, mold material 700' is filled through the bore in the cut-off replica 101' into the open space formed by the impression material 600' inside the impression coping 201' and part of the abutment contact surfaces 243 of the impression coping 201.

Figure 11G:
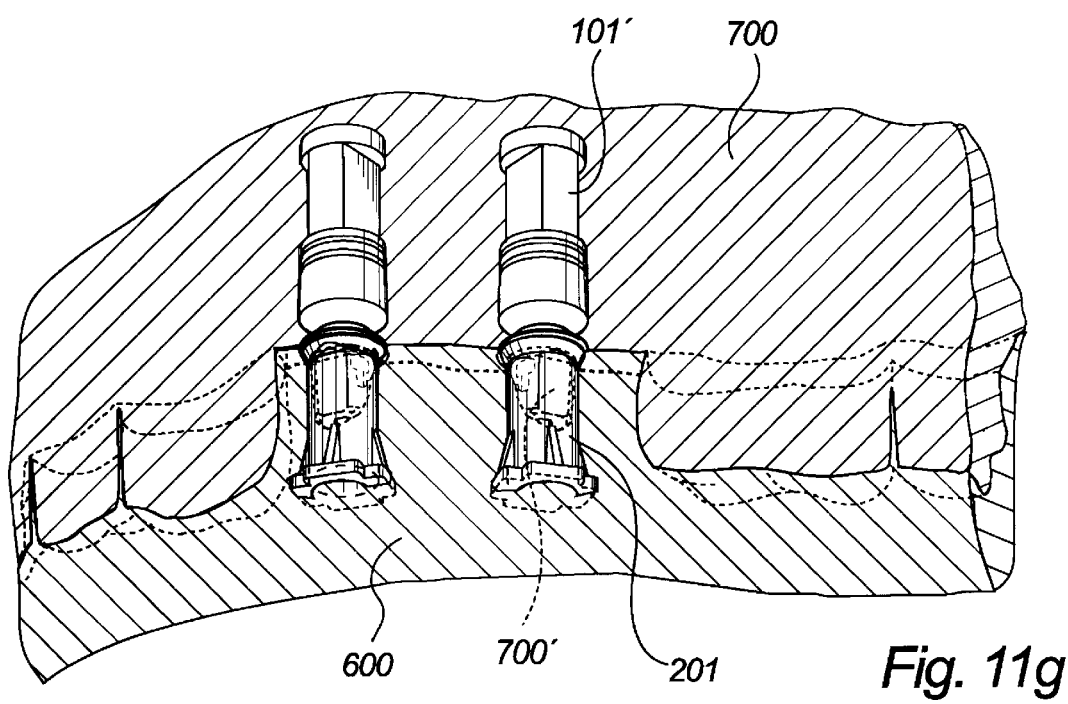

In FIG. 11g, further mold material 700 has been applied to the impression material 600.

Figure 11H:
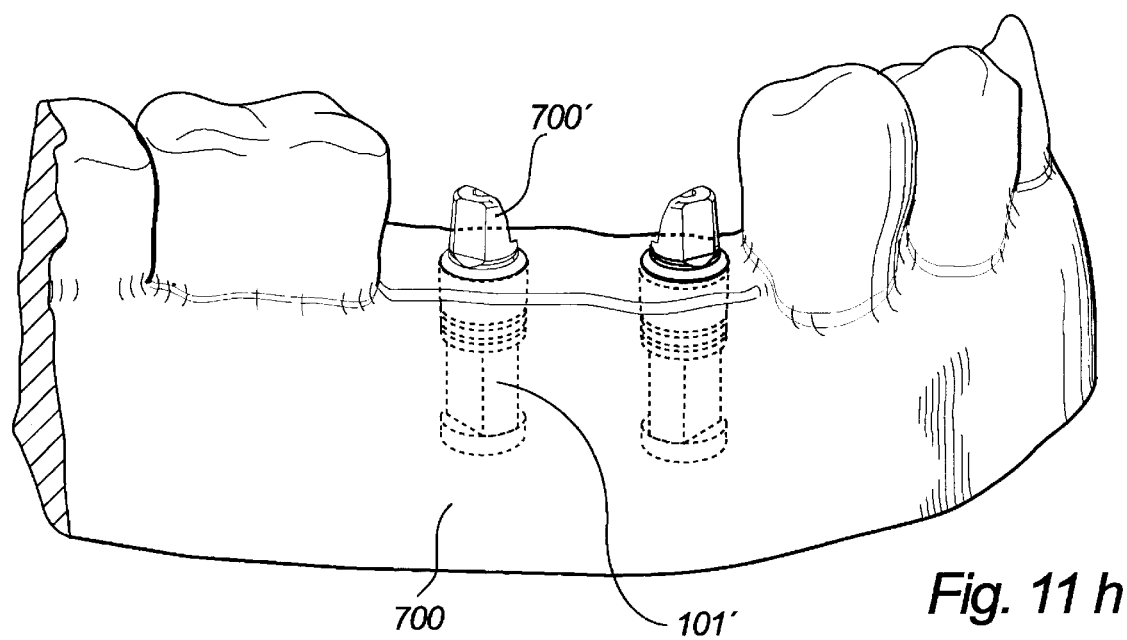

Finally, in FIG. 11h, the impression material 600 and the impression copings 201 have been removed. The molding material 700 now forms a model of the implantation site with the adjacent teeth. The molding material 700' that was filled through the cut-off replicas 101' replicates the upper part of the original modified abutments 1'. However, shoulder parts of the cut-off replicas 101' correspond to the shoulder parts of the original abutments 1 at the implantation site.

Using this model, a proper prosthesis or crown may be manufactured and adjusted, for later installation on the proper abutments 1 at the installation site.

It should be noted how the same abutments, impression copings and abutment replicas may be used both for the standard and the modified procedure.

Other alternatives and embodiments may be considered within the scope of the enclosed patent claims. For example, more than one component engagement means may be arranged on the abutment. In that case, there could possibly be a second component engagement means being provided coronally of the first component engagement means, although said second component engagement means may be destroyed when modifying the abutment. This could still be a functional alternative, providing said first component engagement means would provide the necessary component coupling function. The same applies for the abutment engagement means of the impression cap.

Also, the components described may possibly be consisting of two or more interconnected parts. However, the unitary embodiments described herein are preferred.

The construction of engagement means and rotational locking means may also be varied, as may the outer shape of for example the impression coping, the connection to an implant of the abutment or the apical portion of the abutment replica.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An impression coping for pick-up impression making of a dental abutment attached to a dental implant, said impression coping having a through passage extending from a coronal end to an apical end of the impression coping, said impression coping comprising:
    an abutment surrounding region for surrounding the abutment, wherein said abutment surrounding region has a coronal end, an apical end and an inner wall, said inner wall comprising at least one abutment contact surface for contact with the abutment, and at least one space forming surface for being spaced apart from said abutment in order to provide a space between said space forming surface and the abutment,
    wherein said abutment surrounding region comprises a shoulder contacting portion having an inner wall, and a post contacting portion extending coronally from said shoulder contacting portion and presenting an inner wall forming an angle larger than 180° with said inner wall of said shoulder contacting portion, and said space forming surface and said abutment surface are provided at the inner wall of said post portion.

2. The impression coping according to claim 1, wherein said space forming surface is provided with a vent for passage of air and/or impression material.

3. The impression coping according to claim 1, wherein at least one abutment contact surface tapers inwardly in a coronal direction.

4. The impression coping according to claim 3, wherein said at least one abutment contact surface forms an angle of taper of less than 20° with a longitudinal axis of said impression coping.

5. The impression coping according to claim 4, wherein said angle of taper is less than 15°.

6. The impression coping according to claim 4, wherein said angle of taper is 6°.

7. The impression coping according to claim 4, wherein at least one abutment contact surface is provided with a rotational locking device, for rotational locking of said impression coping on the dental abutment.

8. The impression coping according to claim 1, wherein said rotational locking device is formed by a flat portion of said abutment contact surface.

9. The impression coping according to claim 1, wherein there are at least two abutment contact surfaces arranged to face each other, and two space forming surfaces arranged between said abutment contact surfaces, also facing each other.

10. The impression coping according to claim 1, wherein a prolongation region (241) is provided coronally of said abutment surrounding region, for extension into an impression material.

11. The impression coping according to claim 10, wherein said prolongation region is provided with retention elements for retention of the impression coping in an impression material.

12. The impression coping according to claim 1, further comprising an abutment engagement arranged for releasable engagement with the abutment by linear displacement of said impression coping in relation to the abutment, said abutment engagement being provided apically of at least one space forming surface.

13. The impression coping according to claim 1, further comprising an abutment engagement arranged for releasable engagement with the abutment by linear displacement of said impression coping in relation to the abutment, said abutment engagement being provided apically of at least one space forming surface, wherein said abutment engagement is provided at the post contacting portion, at a position closer to the shoulder contacting portion than to the coronal end of the abutment surrounding region.

14. A set comprising:
    an abutment having a coronal abutment end; and
    a corresponding replica having a coronal replica end, said abutment being provided with a marking for optional shortening of the abutment at a first distance from the coronal abutment end, and wherein said replica is provided with a marking at a second distance from the coronal replica end equal to or less than said first distance.

15. The set according to claim 14, wherein said replica and said abutment are each provided with several markings.

16. A method for making a master cast of a modified standard abutment, comprising the steps of:
    providing an impression of an implant site with an impression coping embedded in impression material, and an open within said impression coping corresposnding to a modified abutment;
    cutting off a coronal portion of a standard abutment replica so as to obtain a remaining part of the abutment replica having a through bore extending there through;
    attaching said remaining part of said abutment replica to said impression coping; and
    pouring mold material through said through bore into the open space corresponding to the modified abutment in the impression material.

17. A method for making a master cast of a modified standard abutment, comprising the steps of:
    attaching an impression coping to said modified abutment being fastened in an implant implanted in bone tissue;
    inserting impression material in said impression coping so as to form an open space corresponding to said modified abutment inside said impression coping;
    adding impression material around the site of said implant so as to embed the impression coping;
    removing the impression material whereby said impression coping is removed with the impression material;
    cutting off a coronal portion of a standard abutment replica to obtain a remaining part of the abutment replica having a through bore extending therethrough;
    attaching said remaining part of said abutment replica to said impression coping;
    pouring mold material through said through bore into the open space corresponding to the modified abutment in the impression material; and
    adding mold material over the entire impression material so as to create a master cast model.

18. An impression coping for pick-up impression making of a dental abutment attached to a dental implant, said impression coping having a through passage extending from a coronal end to an apical end of the impression coping, said impression coping comprising:
    an abutment surrounding region for surrounding the abutment, wherein said abutment surrounding region has a coronal end, an apical end and an inner wall, said inner wall comprising at least two abutment contact surfaces for contact with the abutment, and two space forming surfaces for being spaced apart from said abutment in order to provide a space between said space forming surface and the abutment,
    wherein said at least two abutment contact surfaces are arranged to face each other, and said two space forming surfaces are arranged between said abutment contact surfaces, also facing each other.

19. The impression coping according to claim 18, wherein said space forming surfaces are provided with vents for passage of air and/or impression material.

20. The impression coping according to claim 18, wherein at least one of said at least two abutment contact surfaces tapers inwardly in a coronal direction.

21. The impression coping according to claim 20, wherein at least one of said at least two abutment contact surfaces forms an angle of taper of less than 20° with a longitudinal axis of said impression coping.

22. The impression coping according to claim 21, wherein said angle of taper is less than 15°.

23. The impression coping according to claim 21, wherein said angle of taper is 6°.

24. The impression coping according to claim 18, wherein at least one of said at least two abutment contact surfaces is provided with a rotational locking device, for rotational locking of said impression coping on the dental abutment.

25. The impression coping according to claim 24, wherein said rotational locking device is formed by a flat portion of said abutment contact surface.

26. The impression coping according to claim 18, wherein a prolongation region is provided coronally of said abutment surrounding region, for extension into an impression material.

27. The impression coping according to claim 18, wherein said prolongation region is provided with retention elements for retention of the impression coping in an impression material.

28. The impression coping according to claim 18, further comprising an abutment engagement arranged for releasable engagement with the abutment by linear displacement of said impression coping in relation to the abutment, said abutment engagement being provided apically of at least one of said two space forming surfaces.

29. The impression coping according to claim 28, wherein said abutment engagement is provided at a post contacting portion, at a position closer to the shoulder contacting portion than to the coronal end of the abutment surrounding region.

* * * * *